United States Patent
von der Osten et al.

(10) Patent No.: US 7,098,017 B2
(45) Date of Patent: *Aug. 29, 2006

(54) PROTEASE VARIANTS AND COMPOSITIONS

(75) Inventors: Claus von der Osten, Lyngby (DK); Torben Halkier, Birkerod (DK); Carsten Andersen, Vaerloese (DK); Peter Bauditz, Copenhagen O (DK); Peter Kamp Hansen, Lejre (DK)

(73) Assignee: Novozymes A/S, Bagsvaerd (DK)

( * ) Notice: Subject to any disclaimer, the term of this patent is extended or adjusted under 35 U.S.C. 154(b) by 564 days.

This patent is subject to a terminal disclaimer.

(21) Appl. No.: 09/948,080

(22) Filed: Sep. 6, 2001

(65) Prior Publication Data

US 2002/0102702 A1    Aug. 1, 2002

Related U.S. Application Data

(62) Division of application No. 08/963,851, filed on Nov. 4, 1997, now Pat. No. 6,300,116.

(30) Foreign Application Priority Data

Nov. 4, 1996 (DK) .................................. 1235/96
Nov. 5, 1996 (DK) .................................. 1240/96
Mar. 14, 1997 (DK) ................................. 0284/97

(51) Int. Cl.
*C12N 9/52* (2006.01)
*C12N 9/56* (2006.01)
*C12N 15/57* (2006.01)
*C12N 15/74* (2006.01)
*C11D 3/386* (2006.01)

(52) U.S. Cl. ............... 435/220; 435/69.1; 435/221; 435/222; 435/252.3; 435/320.1; 536/23.2; 510/300

(58) Field of Classification Search .......... 435/221, 435/222, 471, 69.1, 252.3, 320.1, 220; 510/300; 536/23.2

See application file for complete search history.

(56) References Cited

U.S. PATENT DOCUMENTS

| 4,760,025 | A | * | 7/1988 | Estell et al. ............. 510/392 |
| RE34,606 | E | * | 5/1994 | Estell et al. ............. 510/392 |
| 5,324,653 | A | * | 6/1994 | Van Eekelen et al. ...... 435/221 |
| 5,482,849 | A | * | 1/1996 | Branner et al. ........... 435/222 |
| 5,500,364 | A | * | 3/1996 | Christianson et al. ...... 435/221 |
| 5,543,302 | A | | 8/1996 | Boguslawski et al. ..... 435/69.1 |
| 5,665,587 | A | * | 9/1997 | Aaslyng et al. ........... 435/221 |
| 5,700,676 | A | * | 12/1997 | Bott et al. ............... 435/221 |
| 5,741,694 | A | * | 4/1998 | Hastrup et al. ........... 435/222 |
| 5,766,898 | A | * | 6/1998 | Loevborg ................. 510/392 |
| 5,837,517 | A | * | 11/1998 | Sierkstra et al. .......... 435/221 |
| 5,846,802 | A | * | 12/1998 | Buxton et al. ............ 435/225 |
| 6,190,900 | B1 | * | 2/2001 | Sierkstra et al. .......... 435/221 |
| 6,287,841 | B1 | * | 9/2001 | Mulleners et al. ......... 435/221 |
| 6,300,116 | B1 | * | 10/2001 | von der Osten et al. .... 435/220 |
| 6,436,690 | B1 | * | 8/2002 | Brode et al. ............. 435/222 |
| 6,455,295 | B1 | * | 9/2002 | Brode et al. ............. 435/221 |
| 6,475,765 | B1 | * | 11/2002 | Brode et al. ............. 435/221 |
| 6,586,221 | B1 | * | 7/2003 | Graycar et al. ........... 435/219 |
| 6,599,730 | B1 | * | 7/2003 | Brode et al. ............. 435/221 |
| 6,682,924 | B1 | * | 1/2004 | Sierkstra et al. .......... 435/220 |

FOREIGN PATENT DOCUMENTS

| WO | WO 87/05050 |   | 8/1987 |
| WO | WO 89/06279 A1 | * | 7/1989 |
| WO | WO 91/00345 A1 | * | 1/1991 |
| WO | WO 94/02618 A1 | * | 2/1994 |
| WO | WO 95/10615 A1 | * | 4/1995 |
| WO | WO 95/30011 A2 | * | 11/1995 |
| WO | WO 96/28557 A2 | * | 9/1996 |
| WO | WO 96/28558 |   * | 9/1996 |
| WO | WO 96/34964 A2 | * | 11/1996 |

OTHER PUBLICATIONS

Abstract-PCT-WO 96/34946.
Abstract-PCT-WO 91/00345.
Abstract-PCT-WO 89/06279.
WPI/Derwent's abstract, No. 93-223530, week 9328, Abstract of JP, 5146292.
Braxton et al., Biochemistry, vol. 31, pp. 7796-7801, (1992).
Brode et al., The Journal of Biological Chemistry, vol. 269, No. 38. pp. 23538-23543, (1994).

* cited by examiner

Primary Examiner—Nashaat T. Nashed
Assistant Examiner—William W. Moore
(74) Attorney, Agent, or Firm—Elias J. Lambiris

(57) ABSTRACT

The present invention relates to enzymes produced by mutating the genes for a number of subtilases and expressing the mutated genes in suitable hosts are presented. The enzymes exhibit improved autoproteolytic stability in comparison to their wild type parent enzymes.

21 Claims, No Drawings

US 7,098,017 B2

PROTEASE VARIANTS AND COMPOSITIONS

CROSS-REFERENCE TO RELATED APPLICATIONS

This application is a divisional of U.S. application Ser. No. 08/963,851 filed Nov. 4, 1997, now U.S. Pat. No. 6,300,116 and claims priority of Danish application nos. 1235/96, 1240/96 and 0284/97 filed Nov. 4, 1996, Nov. 5, 1996 and Mar. 14, 1997, respectively, the contents of which are fully incorporated herein by reference.

TECHNICAL FIELD

This invention relates to novel mutant protease enzymes or enzyme variants useful in formulating detergent compositions and exhibiting increased autoproteolytic stability; cleaning and detergent compositions containing said enzymes; mutated genes coding for the expression of said enzymes when inserted into a suitable host cell or organism; and such host cells transformed therewith and capable of expressing said enzyme variants.

BACKGROUND OF THE INVENTION

In the detergent industry enzymes have for more than 30 years been implemented in washing formulations. Enzymes used in such formulations comprise proteases, lipases, amylases, cellulases, as well as other enzymes, or mixtures thereof. Commercially most important enzymes are proteases.

Although proteases have been used in the detergent industry for more than 30 years, much remains unknown as to details of how these enzymes interact with substrates and/or other substances present in e.g. detergent compositions. Some factors related to specific residues of the proteases and influencing certain properties, such as oxidative and thermal stability in general, of the proteases have been elucidated, but much remains to be found out. Also, it is still not exactly known which physical or chemical characteristics are responsible for a good washing performance or stability of a protease in a specific detergent composition.

The currently used proteases have for the most part been found by isolating proteases from nature and testing them in detergent formulations.

At present at least the following proteases are known to be commercially available and many of them are marketed in large quantities in many countries of the world.

Subtilisin BPN' or Novo (available from e.g. SIGMA, St. Louis, U.S.A.), and Subtilisin Carlsberg, ALCALASE® (NOVO NORDISK A/S)) and MAXATASE®(Genencor).

A *Bacillus lentus* subtilisin, subtilisin 309, marketed by NOVO NORDISK A/S as SAVINASE®. A protein engineered variant of this enzyme is marketed as DURAZYM®.

Enzymes closely resembling SAVINASE®, such as subtilisin PB92, MAXACAL® marketed by Genencor Inc. (a protein engineered variant of this enzyme is marketed as MAXAPEM®), OPTICLEAN® marketed by SOLVAY et Cie. and PURAFECT® marketed by GENENCOR International.

A *Bacillus lentus* subtilisin, subtilisin 147, marketed by NOVO NORDISK A/S as ESPERASE®;

An increasing number of commercially used proteases are protein engineered variants of naturally occurring wild type proteases, e.g. DURAZYM® (Novo Nordisk A/S), RELASE® (Novo Nordisk A/S), MAXAPEM® (Gist-Brocades N.V.), PURAFECT® (Genencor International, Inc.).

Therefore, an object of the present invention, is to provide improved protein engineered protease variants, especially for use in the detergent industry.

Proteases

Enzymes cleaving the amide linkages in protein substrates are classified as proteases, or (interchangeably) peptidases (see Walsh, 1979, *Enzymatic Reaction Mechanisms*. W.H. Freeman and Company, San Francisco, Chapter 3). Bacteria of the *Bacillus* species secrete two extracellular types of protease, neutral proteases (or metalloproteases), and alkaline proteases among which the most important functionally is a serine endopeptidase and usually referred to as subtilisin.

Serine Proteases

A serine protease is an enzyme which catalyzes the hydrolysis of peptide bonds, and in which there is an essential serine residue at the active site (White, Handler and Smith, 1973 *"Principles of Biochemistry,"* Fifth Edition, McGraw-Hill Book Company, NY, pp. 271–272).

The bacterial serine proteases have molecular weights in the 20,000 to 45,000 Daltons range. They are inhibited by diisopropylfluorophosphate. They hydrolyze simple terminal esters and are similar in activity to eukaryotic chymotrypsin, also a serine protease. A more narrow term, alkaline protease, covering a sub-group, reflects the high pH optimum of some of the serine proteases, from pH 9.0 to 11.0 (for review, see Priest (1977) *Bacteriological Rev.* 41 711–753).

Subtilases

A sub-group of the serine proteases tentatively designated subtilases has been proposed by Siezen et al., *Protein Engng.* 4 (1991) 719–737. They are defined by homology analysis of more than 40 amino acid sequences of serine proteases previously referred to as subtilisin-like proteases. A subtilisin was previously defined as a serine protease produced by Gram-positive bacteria or fungi, and according to Siezen et al. now is a subgroup of the subtilases. A wide variety of subtilisins have been identified, and the amino acid sequence of a number of subtilisins have been determined. These include more than six subtilisins from *Bacillus* strains, namely, subtilisin 168, subtilisin BPN', subtilisin Carlsberg, subtilisin Y, subtilisin amylosacchariticus, and mesentericopeptidase (Kurihara et al. (1972) *J. Biol. Chem.* 247 5629–5631; Wells et al. (1983) *Nucleic Acids Res.* 11 7911–7925; Stahl and Ferrari (1984) *J. Bacteriol.* 159 811–819, Jacobs et al. (1985) *Nucl. Acids Res.* 13 8913–8926; Nedkov et al. (1985) *Biol. Chem. Hoppe-Seyler* 366 421–430, Svendsen et al. (1986) *FEBS Lett.* 196 228–232), one subtilisin from an actinomycetales, thermitase from *Thermoactinomyces vulgaris* (Meloun et al. (1985) *FEBS Lett.* 198 195–200), and one fungal subtilisin, proteinase K from *Tritirachium album* (Jany and Mayer (1985) *Biol. Chem. Hoppe-Seyler* 366 584–492). for further reference Table I from Siezen et al. has been reproduced below.

Subtilisins are well-characterized physically and chemically. In addition to knowledge of the primary structure (amino acid sequence) of these enzymes, over 50 high resolution X-ray structures of subtilisins have been determined which delineate the binding of substrate, transition state, products, at least three different protease inhibitors, and define the structural consequences for natural variation (Kraut (1977) *Ann. Rev. Biochem.* 46 331–358).

One subgroup of the subtilases, I-S1, comprises the "classical" subtilisins, such as subtilisin 168, subtilisin BPN', subtilisin Carlsberg (ALCALASE®, NOVO NORDISK A/S), and subtilisin DY.

A further subgroup of the subtilases I-S2, is recognized by Siezen et al. (supra). Sub-group I-S2 proteases are described as highly alkaline subtilisins and comprise enzymes such as subtilisin PB92 (MAXACAL®, Gist-Brocades NV), subtilisin 309 (SAVINASE®, NOVO NORDISK A/S), subtilisin 147 (ESPERASE®, NOVO NORDISK A/S), and alkaline elastase YaB.

Random and site-directed mutations of the subtilase gene have both arisen from knowledge of the physical and chemical properties of the enzyme and contributed information relating to subtilase's catalytic activity, substrate specificity, tertiary structure, etc. (Wells et al. (1987) *Proc. Natl. Acad. Sci. U.S.A.* 84; 1219–1223; Wells et al. (1986) *Phil. Trans. R. Soc.* Lond.A. 317 415–423; Hwang and Warshel (1987) *Biochem.* 26 2669–2673; Rao et al., (1987) *Nature* 328 551–554.

More recent publications covering this area are Carter et al. (1989) *Proteins* 6 240–248 relating to design of variants that cleave a specific target sequence in a substrate (positions 24 and 64); Graycar et al. (1992) *Annals of the New York Academy of Sciences* 672 71–79 discussing a number of previously published results; and Takagi (1993) *Int. J. Biochem.* 25 307–312 also reviewing previous results.

Especially site-directed mutagenesis of the subtilisin genes has attracted much attention, and various mutations are described in the following patent applications and patents:

Previously Characterized Protease Variants

Numerous references describe construction of Protease variants. In order to make it easier to get an overview of the overall prior art status, the references are ordered in two sections.

Section one deals with references describing the technological background and identification of Protease variants presently not believed to be related to the variants disclosed in the present invention. Those references are mainly included in order to summarize the state of the art within the field of construction of protease variants for different purposes.

Section two deals with references describing identification of Protease variants believed to be of some relevance to the variants of the present invention.

References Summarizing the State of the Art (Section 1):

EP 130756 (GENENTECH)(corresponding to U.S. Reissue Pat. No. 34,606 (GENENCOR)) relating to site specific or randomly generated mutations in "carbonyl hydrolases" and subsequent screening of the mutated enzymes for various properties, such as $k_{cat}/K_m$ ratio, pH-activity profile, and oxidation stability. This publication claims site-specific mutation of subtilisins BPN' in certain specified positions, i.e. $^{-1}$Tyr, $^{32}$Asp, $^{155}$Asn, $^{104}$Tyr, $^{222}$Met, $^{166}$Gly, $^{64}$His, $^{169}$Gly, $^{189}$Phe, $^{33}$Ser, $^{221}$Ser, $^{217}$Tyr, $^{156}$Glu or $^{152}$Ala, to provide for enzymes exhibiting altered properties. Since these positions all except position −1 were known to be involved in the functioning of the enzyme prior to the filing of the application, this application does not contribute to solving the problem of deciding where to introduce mutations in order to obtain enzymes with specific desired properties.

EP 214435 (HENKEL) relating to cloning and expression of subtilisin Carlsberg and two mutants thereof. In this application no reason for mutation of $^{158}$Asp to $^{158}$Ser and $^{161}$Ser to $^{161}$Asp is provided.

In WO 87/04461 (AMGEN) it is proposed to reduce the number of Asn-Gly sequences present in the parent enzyme in order to obtain mutated enzymes exhibiting improved pH and heat stabilities, in the application emphasis is put on removing, mutating, or modifying the $^{109}$Asn and the $^{218}$Asn residues in subtilisin BPN'. No examples are provided for any deletions or for modifying the Gly-residues.

WO 87/05050 (GENEX) discloses random mutation and subsequent screening of a number of mutants of subtilisin BPN' for improved properties. In the application mutations are described in positions $^{218}$Asn, $^{131}$Gly, $^{254}$Thr, $^{166}$Gly, $^{116}$Ala, $^{188}$Ser, $^{126}$Leu, and $^{53}$Ser.

EP 260105 (GENENCOR) describes modification of certain properties in enzymes containing a catalytic triad by selecting an amino acid residue within about 15 Å from the catalytic triad and replace the selected amino acid residue with another residue. Enzymes of the subtilase type described in the present specification are specifically mentioned as belonging to the class of enzymes containing a catalytic triad. In subtilisins positions 222 and 217 are indicated as preferred positions for replacement.

Also, it has been shown by Thomas, Russell, and Fersht (1985) *Nature* 318 375–376 that exchange of $^{99}$Asp into $^{99}$Ser in subtilisin BPN' changes the pH dependency of the enzyme.

In a subsequent article (1987) *J. Mol. Biol.* 193 803–813, the same authors also discuss the substitution of $^{156}$Ser in place of $^{156}$Glu.

Both these mutations are within a distance of about 15 Å from the active $^{64}$His.

In *Nature* 328 496–500 (1987) Russel and Fersht discuss the results of their experiments and present rules for changing pH-activity profiles by mutating an enzyme to obtain changes in surface charge.

WO 88/08028 (Genex) and WO 88/08033 (Amgen) both relate to modifications of amino acid residues in the calcium binding sites of subtilisin BPN'. The enzyme is said to be stabilized by substituting more negatively charged residues for the original ones.

WO 95/27049 (SOLVAY S.A.) describes a subtilisin 309 type protease with the following mutations: N43R+N116R+N117R (BPN' numbering. Data indicate the corresponding variant is having improved stability, compared to wildtype.

WO 95/30011, WO 95/30010, and WO 95/29979 (PROCTER & GAMBLE COMPANY) describe 6 regions, especially position 199–220 (BPN' numbering), in both Subtilisin BPN' and subtilisin 309, which are designed to change (i.e. decrease) the adsorption of the enzyme to surface-bound soils. It is suggested that decreased adsorption by an enzyme to a substrate results in better detergent cleaning performance. No data on any variants or specific detergent wash performance data are provided.

Previously Characterized Protease Variants Having Some Relevance to the Present Invention (Section Two):

In EP 251 446 (GENENCOR) it is described how homology considerations at both primary and tertiary structural levels may be applied to identify equivalent amino acid residues whether conserved or not. It is claimed that this information together with the inventors knowledge of the tertiary structure of subtilisin BPN' brought the inventors to select a number of positions susceptible to mutation with an expectation of obtaining mutants with altered properties.

The positions so identified are: $^{124}$Met, $^{222}$Met, $^{104}$Tyr, $^{152}$Ala, $^{156}$Glu, $^{166}$Gly, $^{169}$Gly, $^{189}$Phe, $^{217}$Tyr. Also $^{155}$Asn, $^{21}$Tyr, $^{22}$Thr, $^{24}$Ser, $^{32}$Asp, $^{33}$Ser, $^{36}$Asp, $^{46}$Gly, $^{48}$Ala, $^{49}$Ser, $^{50}$Met, $^{77}$Asn, $^{87}$Ser, $^{94}$Lys, $^{95}$Val, $^{96}$Leu, $^{107}$Ile, $^{110}$Gly, $^{170}$Lys, $^{171}$Tyr, $^{172}$Pro, $^{197}$Asp, $^{199}$Met, $^{204}$Ser, $^{213}$Lys, and $^{221}$Ser, which positions are identifed as being expected to influence various properties of the enzyme. Also, a number of mutations are exemplified to support these suggestions. In addition to single mutations in these positions the inventors also performed a number of multiple mutations. Further the inventors identify $^{215}$Gly, $^{67}$His, $^{126}$Leu, $^{135}$Leu, and amino acid residues within the segments 97–103, 126–129, 213–215, and 152–172 as having interest, but mutations in any of these positions are not exemplified.

Especially of interest for the purpose of the present invention the inventors of EP 251 446 suggest to substitute $^{170}$Lys (in subtilisin BPN', type I-S1), specifically they suggest to introduce Glu or Arg for the original Lys. It appears that the Glu variant was produced and it was found that it was highly susceptible to autolytic degradation (cf. pages 48, 121, 123 (Table XXI includes an obvious error, but indicates a reduction in autolysis half-time from 86 to 13 minutes) and FIG. 32).

In WO 89/06279 (NOVO NORDISK A/S) position 170 is indicated as interesting and it is suggested to replace the existing residue with Tyr. However, no data are given in respect of such a variant. In WO 91/00345 (NOVO NORDISK A/S) the same suggestion is made, and it is shown that the Tyr variant of position 170 in subtilisin 309 (type I–S2) exhibits an improved wash performance in detergents at a pH of about 8 (variant S003 in Tables III, IV, V, VI, VIII, X). The same substitution in combination with other substitutions in other positions also indicates an improved wash performance (S004, S011–S014, S022–S024, S019, S020, S203, S225, S227 in the same Table and Table VII) all in accordance with the generic concept of said application.

In EP 525 610 A1 (SOLVAY) it is suggested to improve the stability of the enzyme (a type I-S2 subtilase closely related to subtilisin PB92) towards ionic tensides by decreasing the hydrophobicity in certain surface regions thereof. It is suggested to substitute Gln for the Arg in position 164 (170 if using BPN' numbering). No variants comprising this substitution are disclosed in the application.

In WO 94/02618 (GIST-BROCADES N.V.) a number of position 164 (170 if using BPN' numbering) variants of the I-S2 type subtilisin PB92 are described. Examples are provided showing substitution of Met, Val, Tyr, and Ile for the original Arg. Wash performance testing in powder detergents of the variants indicates a slight improvement. Especially for the Ile variant wash performance tests on cacao an improvement of about 20–30% is indicated. No stability data are provided.

In PCT/DK96/00207 (not yet published) a number of protease variants with improved wash performance and/or storage stability is described.

It was found that subtilase variants with improved wash performance can by obtained by substituting one or more amino acid residues situated in, or in the vicinity of a hydrophobic domain of the parent subtilase for an amino acid residue more hydrophobic than the original residue, said hydrophobic domain comprising the residues corresponding to residues I165, Y167, Y171 of BLS309 (in BASBPN numbering), and said residues in the vicinity thereof comprising residues corresponding to the residues E136, G159, S164, R170, A194, and G195 of BLS309 (in BASBPN numbering) (PCT/DK96/00207).

U.S. Pat. No. 5,543,302 describes the identification of important autoproteolytic cleavage site in different wild type proteases (MILEZYME®, SAVINASE®, and ESPERASE®).

The present invention focuses on specific protease variants influencing the position of autoproteolytic cleavage sites in a group of protease variants described in our pending patent application PCT/DK96/00207. The variants of the present invention have surprisingly been found to exhibit an altered autoproteolytic degradation pattern compared to the autoproteolytic degradation pattern described for corresponding wildtype proteases in U.S. Pat. No. 5,543,302.

SUMMARY OF THE INVENTION

It has now surprisingly been found that subtilase variants having modification(s) in one or more amino acid residues situated in positions corresponding to residues P129, P131, E136, G159, S164, I165, Y167, R170, Y171 of BLS309 (in BASBPN numbering), have an altered autoproteolytic degradation pattern, as compared to the corresponding wildtype. The primary alteration is an autolytic cleavage site apparently located between residues 132–133 (in BASBPN numbering (SEQ ID NO: 36).

SAVINASE® is known to have a broad substrate specificity and will upon extensive incubation auto cleavage itself at numerous sites. However the initial 1–5 cleavage sites (primary sites) are of highest relevance for industrial applications of the subtilase proteases.

Said autolytic cleavage site located between residues 132–133 is presently believed to be a new primary autoproteolytic cleavage site. This is presently believed to be the first time that this autoproteolytic cleavage site has been identified, as a primary autoproteolytic cleavage site, in a subtilase protease enzyme. For further details reference is made to a working example herein (vide infra).

Consequently in its first aspect, the present invention relates to a subtilase enzyme variant characterized by being derived from a precursor subtilase enzyme having an autoproteolytic split site between residues 132 and 133 (in BASBPN numbering), which further has been modified by substitution, insertion or deletion at or in one or more of the residues situated in positions corresponding to residues 129, 130, 131, 132, 133, 134, 135, 136 of BLS309 (in BASBPN numbering); whereby said variant exhibits increased autoproteolytic stability relative to said precursor subtilase enzyme.

In a second aspect the invention relates a subtilase enzyme variant characterized by being derived from a precursor subtilase enzyme variant having modification(s) in one or more amino acid residues situated in positions corresponding to residues G159, S164, I165, Y167, R170, Y171 of BLS309 (in BASBPN numbering); which further has been modified by substitution, insertion or deletion at or in one or more of the residues situated in positions corresponding to residues 129, 130, 131, 132, 133, 134, 135, 136 (in BASBPN numbering); whereby said variants exhibit increased autoproteolytic stability relative to the precursor subtilase variant which is not modified at any of said positions 129–136.

U.S. Pat. No. 5,543,302 teaches that SAVINASE® has an autoproteolytic cleavage site located between residues 192–193 (in BASBPN numbering) and suggests to make modifications in a broad region around this site (between residue 180–210) in order to obtain a variant with increased autoproteolytic stability.

The present inventors have confirmed this autoproteolytic site between residues 192–193 (in BASBPN numbering) in both SAVINASE® and SAVINASE® variants having modification(s) in one or more amino acid residues situated in positions corresponding to residues P129, P131, E136, G159, S164, I165, Y167, R170, Y171 of BLS309 (in BASBPN numbering). The present inventors suggest specific modifications (mutations), in the vicinity of the autoproteolytic site between residues 192–193 (in BASBPN numbering), such as S190P, and G193A (in BASBPN numbering).

Such specific mutations are not discussed or indicated in U.S. Pat. No. 5,543,302, where only a rather broad region (between residues 180–210) is described and no specific mutation resulting in increased autoproteolytic stability is disclosed in U.S. Pat. No. 5,453,302.

For further details reference is made to a working example herein (vide infra).

Accordingly, in a third aspect the invention relates to a subtilase enzyme variant characterized by being derived from a precursor subtilase enzyme having an autoproteolytic split site between residues 192 and 193 (in BASBPN numbering), which further has been modified by substitution, insertion or deletion at or in one or more of the residues situated in positions corresponding to residues 189, 190, 191, 192, 193, 194, 195, 196 (in BASBPN numbering); whereby said variant exhibits increased autoproteolytic stability relative to said precursor subtilase enzyme.

In a fourth aspect the invention relates to a subtilase enzyme variant characterized by being derived from a precursor subtilase enzyme variant having modification(s) in one or more amino acid residues situated in positions corresponding to residues residues P129, P131, E136, G159, S164, I165, Y167, R170, Y171 of BLS309 (in BASBPN numbering) which further has been modified by substitution, insertion or deletion at or in one or more of the residues situated in positions corresponding to residues 189, 190, 191, 192, 193, 194, 195, 196 of BLS309 (in BASBPN numbering); whereby said variants exhibit increased autoproteolytic stability relative to the precursor subtilase variant which is not modified at any of said positions 189–196.

In a further aspect the invention relates to DNA constructs capable of expressing the enzymes of the invention, when inserted in a suitable manner into a host cell that subsequently is brought to express the subtilisin enzyme(s) of the first aspect.

In a further aspect the invention relates to the production of the subtilisin enzymes of the invention by inserting a DNA construct according to the second aspect into a suitable host, cultivating the host to express the desired subtilase enzyme, and recovering the enzyme product.

The invention relates, in part, but is not limited to, mutants of the genes expressing the subtilase sub-group I-S2 enzymes and the corresponding enzyme variants, as indicated above.

Other subtilase gene variants encompassed by the invention are such as those of the subtilase subgroup I-S1, e.g. Subtilisin BPN', and Subtilisin Carlsberg genes and ensuing variant Subtilisin BPN', Proteinase K, and Subtilisin Carlsberg enzymes, which exhibit improved stability in concentrated liquid detergents.

Still further subtilase gene variants encompassed by the invention are such as Proteinase K and other genes and ensuing variant Proteinase K, and other subtilase enzymes, which exhibit improved stability in concentrated liquid detergents.

Other examples of parent subtilase enzymes that can be modified in accordance with the invention are listed in Table I.

Further the invention relates to the use of the mutant enzymes in cleaning compositions and cleaning compositions comprising the mutant enzymes, especially detergent compositions comprising the mutant subtilisin enzymes.

According to the invention such detergent compositions may furthermore comprise one or more other enzymes, such as lipases, cellulases, amylases, etc.

| AMINO ACIDS | | | | |
|---|---|---|---|---|
| A | = | Ala | = | Alanine |
| V | = | Val | = | Valine |
| L | = | Leu | = | Leucine |
| I | = | Ile | = | Isoleucine |
| P | = | Pro | = | Proline |
| F | = | Phe | = | Phenylalanine |
| W | = | Trp | = | Tryptophan |
| M | = | Met | = | Methionine |
| G | = | Gly | = | Glycine |
| S | = | Ser | = | Serine |
| T | = | Thr | = | Threonine |
| C | = | Cys | = | Cysteine |
| Y | = | Tyr | = | Tyrosine |
| N | = | Asn | = | Asparagine |
| Q | = | Gln | = | Glutamine |
| D | = | Asp | = | Aspartic Acid |
| E | = | Glu | = | Glutamic Acid |
| K | = | Lys | = | Lysine |
| R | = | Arg | = | Arginine |
| H | = | His | = | Histidine |
| X | = | Xaa | = | Any amino acid |

| NUCLEIC ACID BASES | | | |
|---|---|---|---|
| A | = | | Adenine |
| G | = | | Guanine |
| C | = | | Cytosine |
| T | = | | Thymine (only in DNA) |
| U | = | | Uracil (only in RNA) |

Variants

In describing the various enzyme variants produced or contemplated according to the invention, the following nomenclatures have been adapted for ease of reference:

Original amino acid(s) position(s) substituted amino acid(s)

According to this the substitution of Glutamic acid for glycine in position 195 is designated as:

Gly 195 Glu or G195E a deletion of glycine in the same position is:

Gly 195*or G195* and insertion of an additional amino acid residue such as lysine is:

Gly 195 GlyLys or G195GK

Where a deletion in comparison with the sequence used for the numbering is indicated, an insertion in such a position is indicated as:

*36 Asp or *36D for insertion of an aspartic acid in position 36

Multiple mutations are separated by pluses, i.e.:

Arg 170 Tyr+Gly 195 Glu or R170Y+G195E representing mutations in positions 170 and 195 substituting tyrosine and glutamic acid for arginine and glycine, respectively.

Positions

In describing the variants in this application and in the appended claims use is made of the alignment of various subtilases in Siezen et al., supra. In other publications relating to subtilases other alignments or the numbering of specific enzymes have been used. It is a routine matter for the skilled person to establish the position of a specific residue in the numbering used here. Reference is also made to Table I of WO 91/00345 showing an alignment of residues relevant for the present invention from a number of subtilases.

TABLE I

Presently established Subtilases (from Siezen et al., supra)

| Organism | cDNA | enzyme | acronym gene |
|---|---|---|---|
| PROKARYOTES | | | |
| Bacteria: Gram-positive | | | |
| *Bacillus subtilis* 168 | apr A | subtilisin I168,apr | ABSS168 |
| *Bacillus amyloliquefaciens* | apr | subtilisin BPN' (NOVO) | BASBPN |
| *Bacillus subtilis* DY | – | subtilisin DY | BSSDY |
| *Bacillus licheniformis* | + | subtilisin Carlsberg | BLSCAR |
| *Bacillus lentus* | + | subtilisin 147 | BLS147 |
| *Bacillus alcalophilus* PB92 | + | subtilisin PB92 | BAPB92 |
| *Bacillus* sp. DSM 4828 | – | alkaline protease | BDSM48 |
| *Bacillus* YaB | ale | alkaline elastase YaB | BYSYAB |
| *Bacillus subtilis* 168 | epr | min. extracell. prot. | BSEPR |
| *Bacillus subtilis* | bpf | bacillopeptidase F | BSBPF |
| *Bacillus subtilis* IFO3013 | ispl | intracell.ser. prot.1 | BSISP1 |
| *Bacillus subtilis* A50 | – | intracell.ser. prot. | BSIA50 |
| *Bacillus thuringiensis* | – | extracell. ser. prot. | BTFINI |
| *Bacillus cereus* | – | extracell. ser. prot. | BCESPR |
| *Nocardiopsis dassonvillei* | – | alkaline ser. prot. | NDAPII |
| *Thermoactinomyces vulgaris* | – | thermitase | TVTHER |
| *Enterococcus faecallscylA* | | cytolysin component A | EFCYLA |
| *Staphylococcus epidermidis* | epiP | epidermin lead. prot. | SEEPIP |
| *Streptococcus pyogenes* | scpA | C5a peptidase | SPSCPA |
| *Lactococcus lactis* SK11 | prtP | SK11 cell wall prot. | LLSK11 |
| Bacteria: Gram-neciative | | | |
| *Dichelobacter nodosus* | + | basic protease | DNEBPR |
| *Xanthomonas campestris* | + | extracellular prot. | XCEXPR |
| *Serratia marcescens* | + | extracell. ser. prot. | SMEXSP |
| *Thermus aquaticus* YT-1 | pstl | aqualysin I | TAAQUA |
| Thermus rT41A | + | T41A protease | TRT41A |
| *Vibrio alginolyticus* | proA | protease A | VAPROA |
| *Streptomyces rutgersensis* | – | proteinase D | SRESPD |
| Archaea | | | |
| halophilic strain 172P1 | – | halophil extra. prot. | ARB172 |
| Cyanobacteria | | | |
| *Anabaena variabilis* | prcA | Ca-dependent protease | AVPRCA |
| LOWER EUKARYOTES | | | |
| Fungi | | | |
| *Tritirachium album* Limber | + | proteinase K | TAPROK |
| *Tritirachium album* | + | proteinase R | TAPROR |
| *Tritirachium album* | proT | proteinase T | TAPROT |
| *Aspergillus oryzae* | + | alkaline protease | AOALPR |

TABLE I-continued

Presently established Subtilases (from Siezen et al., supra)

| Organism | cDNA | enzyme | acronym gene |
|---|---|---|---|
| *Malbranchea pulchella* | – | thermomycolin | MPTHMY |
| *Acremonium chrysogenum* | alp | alkaline protease | ACALPR |
| Yeasts | | | |
| *Kluyveromyces lactis* | kex1 | Kex1 ser. proteinase | KLKEX1 |
| *Saccharomyces cerevisiae* | kex2 | Kex2 ser. proteinase | SCKEX2 |
| *Saccharomyces cerevisiae* | prb1 | protease B | SCPRB1 |
| *Yarrowia lipolytica* | xpr2 | alk.extracell. prot. | LXPR2 |
| HIGHER EUKARYOTES | | | |
| Worms | | | |
| *Caenorhabditis elegans* | bli4 | cuticle protease | CEBLI4 |
| Insects | | | |
| Drosophila (fruit fly) | fur1 | furin 1 | DMFUR1 |
| Drosophila (fruit fly) | fur2 | furin 2 | DMFUR2 |
| Plants | | | |
| *Cucumis melo* (melon) | – | cucumisin | CMCUCU |
| Mammals | | | |
| Human (also rat, mouse) | fur | furin | HSFURI |
| Human (also mouse) | + | insulinoma PC2 prot. | HSIPC2 |
| Mouse | + | pituitary PC3 prot. | MMPPC3 |
| Human | + | tripeptidyl peptid.II | HSTPP |

References used for Table I
References to amino acid sequences (GenBank ®/EMBL Data Bank accession numbers are shown in brackets):

ARB172 Kamekura and Seno, (1990) Biochem. Cell Biol. 68 352–359 (amino acid sequencing of mature protease residues 1–35; residue 14 not determined).

BSS168 Stahl. and Ferrari. (1984) J. Bacteriol. 158, 411–418 (K01988). Yoshimoto, Qyama et al. (1488) J. Biochem. 103, 1060–1065 (the mature subtilisin from *B. subtilis* var. *amylosaccharicus* differs in having T13OS and T162S). Svendsen, et al. (1986) FEBS Lell. 196,228–232 (PIR A23624; amino acid sequencing; the mature alkaline mesentericopeptidase From *B. mesentericus* differs in having S85A, A88S, S89A. S183A and N259S).

BASBPN Wells, et al. (1983) Nucl.Acids Res. 11 7911–7925 (X00165). Vasantha et al., (1984) J. Bacteriol. 159 811–814(K02496).

BSSDY Nedkov et al. (1983) Hoppe-Seyler's Z. Physiol. Chem. 364 1537–1540 (PIR A00969; amino acid sequencing).

BLSCAR Jacobs et al. (1985) Nucleic Acids Res. 13 8913–8926 (X03341). Smith et al. (1968) J. Biol. Chem. 243 2184–2191 (PIR A00968; amino acid sequencing; mature protease sequence differs in having TIO3S, P129A, S158N, N161S and S212N).

BLS147 Hastrup et al. (1989) PCT Patent Appl. WO 8906279. Pub. July 13 1989. (ESPERASE ® from *B. lentus*). Takami et al. (1990) Appl. Microbiol. Biotechnol., 33 519–523 (amino acid sequencing of mature alkaline protease residues 1–20 from Bacillus sp. no. AH-101; this sequence differs from BLS147 in having N11S).

BABP92 van der Laan et al. (1991) Appl. Environ. Microbiol. 57 901–909. (Maxacal ®). Hastrup et al. (1989) PCT Patent Appl. WO 8906279. Pub. 13 Jul 1989. (subtilisin 309. SAVINASE from *B. lentus* differs only in having N87S). Godette et al. (1991) Abstracts 5th Protein Society Symposium, June 6, Baltimore: abstract M8 (a high-alkaline protease from *B. lentus* differs in having N87S, S99D, S101R, S103A, V1041 and G159S).

BDSM48 Rettenmaier et al. (1990) PCT Patent Appl. WO 90/04022. Publ.April 19, 1990.

BYSYAB Kaneko et al. (1989) J. Bacteriol. 171 5232–5236 (M28537).

BSEPR Sloma et al. (1988) J. Bacteriol. 170 5557–5563

TABLE I-continued

Presently established Subtilases (from Siezen et al., supra)

| Organism | cDNA enzyme acronym gene |
|---|---|
| BSBPF | (M22407). Bruckner (1990) Mol. Gen. Genet. 221 486–490 (X53307).<br>Sloma et al. (1990) J. Bacteriol. 172 1470–1477 (M29035; corrected). Wu et al. (1990) J. Blot. Chem. 265 6845–6850 (J05400; this sequence differs in having A169V and 586 less C-terminal residues due to a frameshift). |
| BSISPI | Koide et al. (1986) J. Bacteriol. 167 110–116 (M13760). |
| BSIA50 | Strongin et al. (1978) J. Bacteriol. 133 1401–1411 (amino acid sequencing of mature protease residues 1–54; residues 3. 39, 40. 45, 46, 49 and 50 not determined). |
| BTFINI | Chestukhina et al. (1985) Biokhimiya 50 1724–1730 (amino acid sequencing of mature protease residues 1–14 from *B. thuringiensis* variety *israeliensis*, and residues I-16 and 223–243 from variety *finitimus*). Kunitate et al. (1989) Agric. Blot. Chem. 53 3251–3256 (amino acid sequencing of mature protease residues 6–20 from variety *kurstaki*. BTKURS). |
| BCESPR | Chestukhina et al. (1985) Biokhimiya 50 1724–1730 (amino acid sequencing of mature residues I-16 and 223–243). |
| NDAPII | Tsujibo et al. (1990) Agric. Blot. Chem. 54 2177–2179 (amino acid sequencing of mature residues 1–26). |
| TVTHER | Meloun et al. (1985) FEBS Lett. 183 195–200 (P1RA00973; amino acid sequencing of mature protease residues 1–274). |
| EFCYLA | Segarra et al. (1991) Infect. Immun. 59 1239–1246. |
| SEEPIP | Schnell et al. (1991) personal communication (Siezen et al. (supra). |
| SPSCPA | Chen et al. (1990) J. Blot. Chem. 265 3161–3167 (J05224). |
| DNEBPR | Kortt et al. (1991) Abstracts 5th Protein Society Symposium, June 22–26, Baltimore.abstract 576. |
| LLSK11 | Vos etal. (1989) J. Blot. Chem. 264 13579–13585 (J04962). Kok etal. (1988) Appl. Environ. Microbiol. 54 231–238 (M24767; the sequence from strain Wg2 differs in 44 positions, including 18 differences in the protease domain, and a deletion of residues 1617–1676). Kiwaki et al. (1989) Mol.Microbiol. 3 359–369 (X14130; the sequence from strain NCD0763 differs in 46 positions, including 22 in the protease domain, and a deletion of residues 1617-1 676). |
| XCEXPR | Liu et al. (1990) Mol. Gen. Genet. 220 433–440. |
| SMEXSP | Yanagida et al. (1986) J. Bacterlol. 166 937–994 (M13469). |
| TAAQUA | Terada et al. (1990) J. Blot. Chem. 265 6576–658 1(J054″14). |
| TRT41A | McHale et al. (1990) Abstracts 5th Eur. Congr. Biotechn. Christiansen, Munck and Viliadsen (eds), Munksgaard Int. Publishers, Copenhagen. |
| VAPROA | Deane et al. (1989) Gene 76 281–288 (M25499). |
| SRESPD | Lavrenova et al. (1984) Biochemistry USSR. 49 447–454 (amino acid sequencing of residues 1–23; residues 13, 18 and 19 not determined). |
| AVPRCA | Maldener et al (1991) Mol. Gen. Genet. 225 113–120 (the published sequence has 28 uncertain residues near positions 200–210 due to a frameshift reading error). |
| TAPROK | Gunkel and Gassen (1989) Eur. J. Biochem. 179 185–194 (X14688/X14689). Jany et al. (1986) J. Biol. Chem.Hoppe-Seyler 367 87(PIR A24541; amino acid sequencing; mature protease differs in having S745G, SILST2040-208DSL and VNLL264-267FNL). |
| TAPROR | Samal et al. (1990) Mol. Microbiol. 4 1789–1792 (X56116). |
| TAPROT | Samal et al. (1989) Gene 85 329–333. |
| AOALPR | Tatsumi etal. (1989) Mol. Gen. Genet. 219 33–38. Cheevadhanarah et al. (1991) EMBL Data Library (X54726). |
| MPTHMY | Gaucher and Stevenson (1976) Methods Enzymol. 45 415–433 amino acid sequencing of residues 1–28, and heapeptide LSGTSM with active site serine). |
| ACALPR | Isogai et al. (1991) Agric. Blol. Chem. 55 471–477. Stepanov et al. (1986) lnt. J. Biochem. 18 369–375 (amino acid sequencing of residues 1–27: the mature protease differs in having H13[1]Q, R13[2]N and S13[6]A). |
| KLKEX1 | Tanguy-Rougeau, Wesolowski-Louvel and Fukuhara (1988) FEBS left. 234 464–470 (X07038). |
| SCKEX2 | Mizuno et al. (1988) Biochem. Biophys. Res. Commun. 156 246–254(M24201). |
| SCPRB1 | Moehle et al. (1987) Mol. Cell. Biol. 7 4390–4399 (M18097). |
| YLXYPR2 | Davidow etal. (1987) J. Bacterlol. 169 4621–4629 (M17741). Matoba etal. (1988) Mol. Cell Biol. 8 4904–4916 (M23353). |
| CEBL14 | Peters and Rose (1991) The Worm Breeder's Gazette 11 28. |
| DMFUR1 | Roebroek et al. (1991) FEBS Lett. 289 133–137 (X59384). |
| DMFUR2 | Roebroek et al. (1992) 267 17208–17215. |
| CMCUCU | Kaneda et al. (1984) J. Biochem. 95 825–829 (amino acid sequencing of octapeptide NIISGTSM with active site serine). |
| HSFURI | van den Ouweland eta l. (1990) Nucl. Acids Res. 18 664 (X04329) (the sequence of mouse furin differs in 51 positions, including five in the catalytic domain: A15E, Y21F, S223F, A232V and N258 [2]D). Misumi et al.(1990) Nucl. Acids Res. 18 6719 (X55660: the sequence of rat furin differs in 49 positions, including three in the catalytic domain: A15E, Y21F, H24R). |
| HSIPC2 | Smeekens and Steiner (1990) J. Blot. Chem. 265 2997–3000 (J05252). Seidah et al. (1990) DNA Cell Biol. 9 41 5–424 (the sequence of mouse pituitary PC2 protease differs in 23 positions, including seven in the protease domain: 14F, S42[2]Y, E45D, N76S, D133E, V134L and G239[1]D). |
| MMPPC3 | Smeekens et al. (1991) Proc. Natl. Acad. Sd. USA 88 340–344 (M58507). Seidah et al. (1990) DNA Cell Blot. 9 415–424 (M55668/M55669; partial sequence). |
| HSTPP | Tomkinson and Jonsson (1991) Biochemistry 30 168–174 (J05299). |

Definitions

Prior to discussing this invention in further detail, the following terms will first be defined.

"Altered autolytic stability" or "altering autolytic stability" is intended to mean increasing or decreasing the autolytic stability compared to that of the original protease.

"Altered autoproteolytic degradation sites" are intended to indicate altered autoproteolytic degradation sites over those of the original protease. The alteration may be a formation of a completely new site or the removal of a site in the original protease. The term "altered autoproteolytic degradation sites" is also intended to indicate alterations where an autoproteolytic site which is not a e.g. primary or secondary cleavage site in the original protease after alteration of the degradation pattern turns out to a e.g. a primary or a secondary autoproteolytic site.

"Autoproteolytic cleavage site" is used to indicate a site of the protease where the autoproteolysis of the protease is believed to take place. This site could e.g. be defined as being located between amino acid residues X and Y.

Cleavage sites can be identified by preparing an aqueous solution of a protease; rapidly inactivating the protease to prevent progressive degradation of peptide fragments produced by autolysis; separating the peptide fragments under conditions which prevent reactivation of the protease; and identifying the N-terminal amino acids of the separated fragments. For further details reference is made to a working example herein (vide infra).

The term "autoproteolytic cleavage site" may alternatively be called "autoproteolytic split site".

"Primary autoproteolytic cleavage site" is intended to mean the first 1–5 initial cleavage site(s) where the protease auto cleavage itself.

"Modification(s) of a subtilase variant". The term "modification(s)" used in connection with modification(s) of a subtilase variant as discussed herein is defined to include chemical modification as well as genetic manipulation to reduce the rate of autolytic degradation. The modification(s) can be by substitution, deletion and/or insertions in or at the amino acid(s) of interest.

When the term "modification(s)" is used in connection with substitutions, deletion and/or insertions at or in the vicinity of an autolytic cleavage site it is defined to include modification(s) to reduce the rate of autolytic degradation. Modification should occur at or in the vicinity of the amino acids which comprise the susceptible polypeptide bond of those amino acids. The phrase "in the vicinity of" is defined herein to mean within three amino acids upstream or downstream of those amino acids forming the susceptible bond.

"Random mutagenesis". is intended to be understood in a conventional manner, i.e. to indicate an introduction of one or more mutations at random positions of the parent enzyme or introduction of random amino acid residues in selected positions or regions of the parent enzyme. The random mutagenesis is normally accompanied by a screening which allows to select for mutated enzymes which, as compared with the parent enzyme, has improved properties. Suitable techniques for introducing random mutations and screening for improved properties are discussed in further detail herein.

"Wash performance" means the ability of an enzyme to catalyze the degradation of various naturally occurring substrates present on the objects to be cleaned during e.g. wash is often referred to as its washing ability, washability, detergency, or wash performance. Throughout this application the term wash performance will be used to encompass this property.

"SAVINASE®" is marketed by NOVO NORDISK A/S. It is subtilisin 309 from *B. lentus* and differs from BABP92 only in having N87S (see Table I herein).

"Precursor subtilase" is a subtilase defined according to Siezen et al. (Protein Engineering 4:719–737 (1991)). For further details see section named "SUBTILASES" described herein. A precursor subtilase may also be a subtilase isolated from a natural source, wherein subsequent modification have been made while retaining the characteristic of a subtilase.

"Substrate" used in connection with a substrate for a protease should be interpreted in its broadest form as comprising a compound containing at least one peptide bond susceptible to hydrolysis by a subtilisin protease.

"Product" used in connection with a product derived from a protease enzymatic reaction should in the context of this invention be interpreted to include the products of a hydrolysis reaction involving a subtilisin protease. A product may be the substrate in a subsequent hydrolysis reaction.

"Subtilase variant" or "mutated subtilase" means a subtilase that has been produced by an organism which is expressing a mutant gene derived from a parent microorganism which possessed an original or parent gene and which produced a corresponding parent enzyme, the parent gene having been mutated in order to produce the mutant gene from which said mutated subtilisin protease is produced when expressed in a suitable host.

DETAILED DESCRIPTION OF THE INVENTION

Subtilase variants which have an altered autoproteolytic degradation pattern:

According to the invention any precursor subtilase having a primary autoproteolytic site located at or close to residues 132–133 (in BASBPN numbering), will exhibit increased autolytic stability by being modified by substitutions at or in the vicinity (between residue 129–136) of said autolytic cleavage site located between residues 132–133 (in BASBPN numbering).

According to the invention a precursor subtilase having such a primary autolytic cleavage site located between residues 132–133 (in BASBPN numbering), can be a subtilase variant or a wildtype subtilase. The wildtype subtilase may be any of those indicated in Table I having the above specified cleavage site. The subtilase variant may be but is not limited to the variant discussed in Table II. It is presently believed that other subtilase variants than those discussed in Table II may also have a primary autolytic cleavage site located between residues 132 and 133 (in BASBPN numbering).

According to the invention a subtilase variant having modification(s) in one or more of the amino residues mentioned below (See Table II) results in altered autoproteolytic degradation sites, preferably a new primary autoproteolytic site located at or close to residues 132–133 (in BASBPN numbering).

According to the invention a subtilase variant having one or more modification(s) in any of the amino acid residues shown in Table II will exhibit increased autolytic stability by being modified by substitutions at or in the vicinity (between residue 129–136) of said autolytic cleavage site located between residues 132–133 (in BASBPN numbering).

A subtilase variant having one or more modification(s) in any of the amino acid residues shown in Table II, will exhibit increased autolytic stability too by being modified by substitutions at or in the vicinity (between residue 190–196) of the autolytic cleavage site located between residues 192–193 (in BASBPN numbering) and according to the invention a mutual benefit can be obtained by combining modifications in the vicinity around of both the autoproteolytic degradation sites between 132–133 and 192–193.

TABLE II

Residues which when modified give rise to a subtilase variant with an altered autoproteolytic degradation pattern:

| Pos\Enz. | BASBPN | BLSCAR | BLS309 | BLS147 | TVTHER |
|---|---|---|---|---|---|
| 129 | P | P | P | T | T |
| 131 | G | G | P | G | G |
| 136 | K | K | E | E | Q |
| 159 | S | S | G | Q | T |
| 164 | T | T | S | G | A |
| 165 | V | I | I | V | P |
| 167 | Y | Y | Y | Y | Y |
| 170 | K | K | R | R | Y |
| 171 | Y | Y | Y | Y | Y |

Further Table III illustrates the specific amino acid residues in the vicinity of the mentioned autolytic cleavage site located between residues 132–133 (In BASBPN numbering). It is obvious that such a similar or larger tables covering other subtilases may easily be produced by the skilled person.

TABLE III

Residues in the vicinity of the autoproteolytic site located between residue 132–133: (In BASBPN numbering).

| Pos\Enz. | BASBPN | BLSCAR | BLS309 | BLS147 | TVTHER |
|---|---|---|---|---|---|
| 129 | P | P | P | T | T |
| 130 | S | S | S | S | V |
| 131 | G | G | P | G | G |
| 132 | S | S | S | S | N |
| 133 | A | T | A | S | S |
| 134 | A | A | T | T | G |
| 135 | L | M | L | L | L |
| 136 | K | K | E | E | Q |

A similar table illustrating residues in the vicinity of the autoproteolytic site located between residue 192–193 could easily be made by a person skilled in the art.

Consequently the invention relates to subtilase variants having modifications in one or more of the amino residues illustrated in Table II in which the amino acid sequence further has been modified at one or more of the amino acid residue in the vicinity of the autoproteolytic site located between positions 132–133 (in BASBPN numbering) (i.e. positions 129, 130, 131, 132, 133, 134, 135, 136); or Subtilase variants having modifications in one or more of the amino residues illustrated in Table II which further been modified in the vicinity of the autoproteolytic site located between positions 192–193 (in BASBPN numbering) (i.e. positions 190, 191, 192, 193, 194, 195, 196); or Subtilase variants having modifications in one or more of the amino residues illustrated in Table II which further have been modified in the vicinity of both of the two autoproteolytic sites mentioned immediately above.

According to the invention a number of specific modifications in the vicinity of both the autoproteolytic sites located between 132–133 and 192–193 (in BASBPN numbering) or each of the sites will provide increased autoproteolytic stability of the subtilase.

In principle the modification may be a replacement of an amino acid residue located in the vicinity of the cleavage site with any of the other 19 possible amino acid residues resulting in an increased autoproteolytic stability of the resulting variant. Similarly, the modification may be an insertion of one or more of any of the 20 possible amino acid residues in the vicinity of the cleavage site resulting in an increased autoproteolytic stability of the resulting variant. Further the modification may be a deletion of any of the amino acid residue located in the vicinity of the cleavage site resulting in an increased autoproteolytic stability of the resulting variant.

A strategy to identify the specific modifications giving rise to increased autoproteolytic stability is to make localized random mutagenesis in the whole region in the vicinity of one of the site and/or both of the sites (e.g. localized random mutagenesis in all residues between 129–136 and/or 189–196) followed by a screening assay to identify the specific modifications giving rise to increased stability. For illustration of this strategy reference is made to working examples herein (vide infra).

A number of specific mutations, giving rise to increased autoproteolytic stability, are indicated herein (See section "B" and "C" below).

By e.g. looking at Table II or III and applying the principle of the invention a number of candidates for subtilase variants with increased autoproteolytic stability becomes clear.

For both precursor subtilase variants of BASBPN and BLSCAR having an autoproteolytic split site between residues 132–133 (in BASBPN numbering) it is appropriate to make substitutions in any of the positions in the vicinity of this autoproteolytic site in order to make variants with increased autoproteolytic stability.

In the context of this invention a subtilase is defined in accordance with Siezen et al. supra. In a more narrow sense, applicable to many embodiments of the invention, the subtilases of interest are those belonging to the subgroups I-S1 and I-S2. In a more specific sense, many of the embodiments of the invention relate to serine proteases of gram-positive bacteria which can be brought into substantially unambiguous homology in their primary structure, with the subtilases listed in Table I above.

The present invention also comprises any one or more substitutions in the above mentioned positions in combination with any other substitution, deletion or addition to the amino acid sequence of the parent enzyme. Especially combinations with other substitutions known to provide improved properties to the enzyme are envisaged.

Such combinations comprise the positions: 222 (improve oxidation stability), 218 (improves thermal stability), substitutions in the Ca-binding sites stabilising the enzyme, e.g. position 76, and many other apparent from the prior art.

Furthermore combinations with the variants mentioned in EP 405 901 are also contemplated specifically.

Variants

A: Single Variants with an Altered Autoproteolytic Cleavage Site Between 132–133: (in BASBPN Numbering).

The single variants comprise one or more of the mutations mentioned below: Subtilisin BPN', Subtilisin Carlsberg, Subtilisin 168, and Subtilisin DY variants:

A129V, A129I, A129L, A129M, A129F,
G131V, G131I, G131L, G131M, G131F,
K136V, K136I, K136L, K136M, K136F,
S159V, S159I, S159L, S159M, S159F,
T164V, T164I, T164L, T164M, T164F,
Y167V, Y167I, Y167L, Y167M, Y167F,
K170V, K170I, K170L, K170M, K170F,
Y171V, Y171I, Y171L, Y171M, Y171F.

Thermitase Variants:
A129V, A129I, A129L, A129M, A129F,
G131V, G131I, G131L, G131M, G131F,
Q136V, Q136I, Q136L, Q136M, Q136F,
T159V, T159I, T159L, T159M, T159F,
A164V, A164I, A164L, A164M, A164F,
Y167V, Y167I, Y167L, Y167M, Y167F,
Y171V, Y171I, Y171L, Y171M, Y171 F,
Y170V, Y170I, Y170L, Y170M, Y170F.

Subtilisin 309, Subtilisin 147, and Bacillus PB92 protease variants:
T129V, T129I, T129L, T129M, T129F,
G131V, G131I, G131L, G131M, G131F,
E136V, E136I, E136L, E136M, E136F,
G159V, G159I, G159L, G159M, G159F,
G164V, G164I, G164L, G164M, G164F, (BLS147)
S164V, S164I, S164L, S164M, S164F, (BLS309 AND BAPB92)
Y167A, Y167H, Y167N, Y167P, Y167C, Y167W, Y167Q, Y167S, Y167T, Y167G,
Y167V, Y167I, Y167L, Y167M, Y167F
R170W, R170A, R170H, R170N, R170P, R170Q, R170S, R170T, R170Y (disclaimed for BLS309), R170V (disclaimed for BAPB92), R170I (disclaimed for BAPB92), R170L, R170M (disclaimed for BAPB92), R170F, R170G, R170C,

Y171A, Y171H, Y171N, Y171P, Y171C, Y171W, Y171Q, Y171S, Y171T, Y171G,

Y171V, Y171I, Y171L, Y171M, Y171F.

B: Variants Modified in the Vicinity of the Autoproteolytic Cleavage Site Located Between Positions 132–133.

Any of the single variant mentioned under section "A:" above which further comprise one or more of any of the following mutations:
P129D, P129E, P129A (BLS309)
S130D, S130E, S130A (BLS309)
P131G, P131D, P131A (BLS309)
S132C, S132A, S132P (BLS309)
A133P (BLS309)
T134C, T134P, T134A (BLS309)
L135P, L135A (BLS309)
E136A, E136P, E136K (BLS309)
V104C+S132C (BLS309)
V104C+T134C (BLS309)
A108C+T134C (BLS309)

C: Variants Modified in the Vicinity of the Autoproteolytic Cleavage Site Located Between Positions 192–193.

Any of the single variant mentioned under section "A:" above which further comprise one or more of any of the following mutations:
F189A, F189G, F189D, F189R, F189Y, F189E, F189N (BLS309)
S190P, S190D, S190T (BLS309)
Q191S, Q191T, Q191N, Q191A, 0191L, Q191D, Q191W (BLS309)
Y192A, Y192P, Y192D, Y192E, Y192V (BLS309)
G193A, G193N, G193P (BLS309)
A194P, A194D (BLS309) G195E (BLS309)
L196A (BLS309)

D: Variants Modified in the Vicinity of Both the Autoproteolytic Cleavage Sites Located Between Positions 132–133 and 192–193.

Any of the single variant mentioned under section "A:" above which further comprise a combination of one or more of any of the mutations mentioned under section "B" and/or one or more of any of the mutations mentioned under section "C" above.

E: Further Combination Variants:

Any of the above variants mentioned under section "B", "C", and/or "D" are contemplated to prove advantageous if combined with other mutations in any of the positions: 27, 36, 57, 76, 97, 101, 104, 120, 123, 206, 218, 222, 224, 235 and 274.

Specifically the mutations in the following BLS309 and BAPB92 variants are considered appropriate for combination:
K27R, *36D, S57P, N76D, G97N, S101G, V104A, V104N, V104Y, H120D, N123S, A194P, Q206E, N218S, M222S, M222A, T224S, K235L and T274A.

Also such variants comprising any one or two of the substitutions X167V, X167M, X167F, X167L, X167I, X170V, X170M, X170F, X170L, and/or X170I in combination with any one or more of the other substitutions, deletions and/or insertions mentioned above are considered advantageous to combine with any of the mutations mentioned under section "A", "B" and/or "C".

Furthermore variants comprising any of the mutations V104N+S101G, K27R+V104Y+N123S+T274A, or N76D+ V104A or other combinations of these mutations (V104N, S101 G, K27R, V104Y, N123S, T274A, N76D, V104A), in combination with any one or more of the substitutions, deletions and/or insertions mentioned above under section "A", "B", and/or "C" are deemed to exhibit improved properties.

Specific combinations to be mentioned are:

| | |
|---|---|
| A: | Y167I + R170L + A133P |
| B: | Y167I + R170L + T134P |
| C: | Y167I + R170L + A133P + T134P |
| D: | Y167I + R170L + V140C + S132C |
| E: | Y167I + R170L + A108C + T134C |
| F: | Y167A + R170S + F189A |
| G: | Y167A + R170S + Y192A |
| H: | Y167A + R170S + Y192P |
| I: | Y167A + R170S + Y192A + A194P |
| J: | Y167A + R170S + Y192P + A194P |
| K: | Y167A + R170S + F189G |
| L: | Y167A + R170S + F189E |
| M: | Y167A + R170S + F189R |
| N: | Y167I + R170L |
| M: | Y167I + R170L + A194P |
| 0: | Y167A + R170S + A194P |
| P: | Y167A + R170L + A194P |
| Q: | Y167A + R170N + A194P |
| R: | V104C + S132C + Y167I + R170L |
| S: | A108C + T134C + Y167I + R170L |
| T: | V104C + S132C + Y167A + R170S |
| U: | V104C + S132C + Y167A + R170L |
| V: | V104C + S132C + Y167A + R170N |
| X: | A133D + Y167I + R170L |
| Y: | P129K + Y167I + R170L |
| Z: | A133P + Y167A + R170S + A194P |
| AA: | T134P + Y167A + R170S + A194P |
| BB: | A133P + T134P + Y167A + R170S + A194P |
| CC: | A133P + Y167A + R170N + A194P |
| DD: | T134P + Y167A + R170N + A194P |
| EE: | A133P + T134P + Y167A + R170N + A194P |
| FF: | A133P + Y167A + R170L |
| GG: | P129K + P131H + Y167I + R170L |
| HH: | A133P + Y167A + R170S |
| II: | A133P + Y167A + R170N |
| JJ: | Y167A + R170S + F189K |
| KK: | V104C + T134C + Y167A + R170S |

Method for Producing Mutations in Subtilase Genes

Many methods for introducing mutations into genes are well known in the art. After a brief discussion of cloning subtilase genes, methods for generating mutations in both random sites, and specific sites, within the subtilase gene will be discussed.

Cloning a Subtilase Gene

The gene encoding a subtilase may be cloned from any of the organisms indicated in Table I, especially gram-positive bacteria or fungus, by various methods, well known in the art. First a genomic, and/or cDNA library of DNA must be constructed using chromosomal DNA or messenger RNA from the organism that produces the subtilase to be studied. Then, if the amino-acid sequence of the subtilase is known, homologous, labelled oligonucleotide probes may be synthesized and used to identify subtilisin-encoding clones from a genomic library of bacterial DNA, or from a cDNA library. Alternatively, a labelled oligonucleotide probe containing sequences homologous to subtilase from another strain of bacteria or organism could be used as a probe to identify subtilase-encoding clones, using hybridization and washing conditions of lower stringency.

Yet another method for identifying subtilase-producing clones would involve inserting fragments of genomic DNA into an expression vector, such as a plasmid, transforming protease-negative bacteria with the resulting genomic DNA library, and then plating the transformed bacteria onto agar containing a substrate for subtilase, such as skim milk. Those bacteria containing subtilase-bearing plasmid will produce colonies surrounded by a halo of clear agar, due to digestion of the skim milk by excreted subtilase.

Generation of Random Mutations in the Subtilase Gene

Once the subtilase gene has been cloned into a suitable vector, such as a plasmid, several methods can be used to introduce random mutations into the gene.

For instance, the random mutagenesis may be performed by use of a suitable physical or chemical mutagenizing agent, by use of a suitable oligonucleotide, or by subjecting the DNA sequence to PCR generated mutagenesis. Furthermore, the random mutagenesis may be performed by use of any combination of these mutagenizing agents.

The mutagenizing agent may, e.g., be one which induces transitions, transversions, inversions, scrambling, deletions, and/or insertions.

Examples of a physical or chemical mutagenizing agent suitable for the present purpose includes ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used the mutagenesis is typically performed by incubating the DNA sequence encoding the parent enzyme to be mutagenized in the presence of the mutagenizing agent of choice under suitable conditions for the mutagenesis to take place, and selecting for mutated DNA having the desired properties.

When the mutagenesis is performed by the use of an oligonucleotide, the oligonucleotide may be doped or spiked with the three non-parent nucleotides during the synthesis of the oligonucleotide at the positions wanted to be changed. The doping or spiking may be done so that codons for unwanted amino acids are avoided. The doped or spiked oligonucleotide can be incorporated into the DNA encoding the protease enzyme by any published technique using e.g. PCR, LCR or any DNA polymerase and ligase.

When PCR generated mutagenesis is used either a chemically treated or non-treated gene encoding a parent protease enzyme is subjected to PCR under conditions that increases the misincorporation of nucleotides (Deshler 1992, Leung et al. 1989).

A mutator strain of *E. coli* (Fowler et al. 1974), *S. cereviciae* or any other microbial organism may be used for the random mutagenesis of the DNA encoding the protease enzyme by e.g. transforming a plasmid containing the parent enzyme into the mutator strain, growing the mutator strain with the plasmid and isolating the mutated plasmid from the mutator strain. The mutated plasmid may subsequently be transformed into the expression organism.

The DNA sequence to be mutagenized may conveniently be present in a genomic or cDNA library prepared from an organism expressing the parent protease enzyme. Alternatively, the DNA sequence may be present on a suitable vector such as a plasmid or a bacteriophage, which as such may be incubated with or otherwise exposed to the mutagenizing agent. The DNA to be mutagenized may also be present in a host cell either by being integrated in the genome of said cell or by being present on a vector harboured in the cell. Finally, the DNA to be mutagenized may be in isolated form. The DNA sequence to be subjected to random mutagenesis is preferably a cDNA or a genomic DNA sequence.

The random mutagenesis may advantageously be located to a part of the parent protease in question. This may, e.g., be advantageous when a certain region of the enzyme has been identified to be of particular importance for a given property of the enzyme, and which, when modified, is expected to result in a variant having improved properties. Such region may normally be identified when the tertiary structure of the parent enzyme has been elucidated and related to the function of the enzyme.

The localized random mutagenesis is conveniently performed by use of PCR generated mutagenesis techniques as described above or any other suitable technique known in the art.

Alternatively, the DNA sequence encoding the part of the DNA sequence to be modified may be isolated, e.g. by being inserted into a suitable vector, and said part may subsequently be subjected to mutagenesis by use of any of the mutagenesis methods discussed above.

The localized random mutagenesis may be performed in one or more of these regions, and is preferably performed in at least two of the regions.

Generation of Site Directed Mutations in the Subtilase Gene

Once the subtilase gene has been cloned, and desirable sites for mutation identified and the residue to substitute for the original ones have been decided, these mutations can be introduced using synthetic oligonucleotides. These oligonucleotides contain nucleotide sequences flanking the desired mutation sites; mutant nucleotides are inserted during oligonucleotide synthesis. In a preferred method, Site-directed mutagenesis is done by the "Unique site elimination (USE)" or the "Uracil-USE" technique described respectively by Deng et al. (Anal. Biochem. 200:81–88 (1992)) and Markvardsen et al. (BioTechniques 18(3):371–372 (1995)).

Recombinant Expression Vectors

A recombinant vector comprising a DNA construct encoding the enzyme of the invention may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome in part or in its entirety and replicated together with the chromosome(s) into which it has been integrated.

The vector is preferably an expression vector in which the DNA sequence encoding the enzyme of the invention is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the enzyme.

The promoter may be any DNA sequence which shows transcriptional activity in the host cell of choice and may be derived from genes encoding proteins either homologous or heterologous to the host cell.

Examples of suitable promoters for use in bacterial host cells include the promoter of the *Bacillus stearothermophilus* maltogenic amylase gene, the *Bacillus licheniformis* alpha-amylase gene, the *Bacillus amyloliquefaciens* alpha-amylase gene, the *Bacillus subtilis* alkaline protease gen, or the *Bacillus pumilus* xylosidase gene, or the phage Lambda $P_R$ or $P_L$ promoters or the *E. coli* lac, trp or tac promoters.

The DNA sequence encoding the enzyme of the invention may also, if necessary, be operably connected to a suitable terminator.

The recombinant vector of the invention may further comprise a DNA sequence enabling the vector to replicate in the host cell in question.

The vector may also comprise a selectable marker, e.g. a gene the product of which complements a defect in the host cell, or a gene encoding resistance to e.g. antibiotics like kanamycin, chloramphenicol, erythromycin, tetracycline, spectinomycine, or the like, or resistance to heavy metals or herbicides.

To direct an enzyme of the present invention into the secretory pathway of the host cells, a secretory signal sequence (also known as a leader sequence, prepro sequence or pre sequence) may be provided in the recombinant vector. The secretory signal sequence is joined to the DNA sequence encoding the enzyme in the correct reading frame. Secretory signal sequences are commonly positioned 5' to the DNA sequence encoding the enzyme. The secretory signal sequence may be that normally associated with the enzyme or may be from a gene encoding another secreted protein.

The procedures used to ligate the DNA sequences coding for the present enzyme, the promoter and optionally the terminator and/or secretory signal sequence, respectively, or to assemble these sequences by suitable PCR amplification schemes, and to insert them into suitable vectors containing the information necessary for replication or integration, are well known to persons skilled in the art (cf., for instance, Sambrook et al., op. cit.).

Host Cell

The DNA sequence encoding the present enzyme introduced into the host cell may be either homologous or heterologous to the host in question. If homologous to the host cell, i.e. produced by the host cell in nature, it will typically be operably connected to another promoter sequence or, if applicable, another secretory signal sequence and/or terminator sequence than in its natural environment. The term "homologous" is intended to include a DNA sequence encoding an enzyme native to the host organism in question. The term "heterologous" is intended to include a DNA sequence not expressed by the host cell in nature. Thus, the DNA sequence may be from another organism, or it may be a synthetic sequence.

The host cell into which the DNA construct or the recombinant vector of the invention is introduced may be any cell which is capable of producing the present enzyme and includes bacteria, yeast, fungi and higher eukaryotic cells.

Examples of bacterial host cells which, on cultivation, are capable of producing the enzyme of the invention are gram-positive bacteria such as strains of *Bacillus*, such as strains of *B. subtilis, B. licheniformis, B. lentus, B. brevis, B. stearothermophilus, B. alkalophilus, B. amyloliquefaciens, B. coagulans, B. circulans, B. lautus, B. megatherium* or *B. thuringiensis*, or strains of *Streptomyces*, such as *S. lividans* or *S. murinus*, or gram-negative bacteria such as *Echerichia coli*. The transformation of the bacteria may be effected by protoplast transformation, electroporation, conjugation, or by using competent cells in a manner known per se (cf. Sambrook et al., supra).

When expressing the enzyme in bacteria such as *E. coli*, the enzyme may be retained in the cytoplasm, typically as insoluble granules (known as inclusion bodies), or may be directed to the periplasmic space by a bacterial secretion sequence. In the former case, the cells are lysed and the granules are recovered and denatured after which the enzyme is refolded by diluting the denaturing agent. In the latter case, the enzyme may be recovered from the periplasmic space by disrupting the cells, e.g. by sonication or osmotic shock, to release the contents of the periplasmic space and recovering the enzyme.

When expressing the enzyme in gram-positive bacteria such as Bacillus or Streptomyces strains, the enzyme may be retained in the cytoplasm, or may be directed to the extracellular medium by a bacterial secretion sequence. In the latter case, the enzyme may be recovered from the medium as described below.

Method of Producing Subtilase

The present invention provides a method of producing an isolated enzyme according to the invention, wherein a suitable host cell, which has been transformed with a DNA sequence encoding the enzyme, is cultured under conditions permitting the production of the enzyme, and the resulting enzyme is recovered from the culture.

As defined herein, an isolated polypeptide (e.g. an enzyme) is a polypeptide which is essentially free of other non-subtilase polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE.

The term "isolated polypeptide" may alternatively be termed "purified polypeptide".

When an expression vector comprising a DNA sequence encoding the enzyme is transformed into a heterologous host cell it is possible to enable heterologous recombinant production of the enzyme of the invention.

Thereby it is possible to make a highly purified subtilase composition, characterized in being free from homologous impurities.

In this context homologous impurities means any impurities (e.g. other polypeptides than the enzyme of the invention) which originate from the homologous cell where the enzyme of the invention is originally obtained from.

The medium used to culture the transformed host cells may be any conventional medium suitable for growing the host cells in question. The expressed subtilase may conveniently be secreted into the culture medium and may be recovered therefrom by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like.

Detergent Compositions Comprising the Mutant Enzymes

The present invention also comprises the use of the mutant enzymes of the invention in cleaning and detergent compositions and such compositions comprising the mutant subtilisin enzymes. Such cleaning and detergent compositions are described in further details below.

Detergent Disclosure and Examples

Surfactant System

The detergent compositions according to the present invention comprise a surfactant system, wherein the surfactant can be selected from nonionic and/or anionic and/or cationic and/or ampholytic and/or zwitterionic and/or semipolar surfactants.

The surfactant is typically present at a level from 0.1% to 60% by weight.

The surfactant is preferably formulated to be compatible with enzyme components present in the composition. In liquid or gel compositions the surfactant is most preferably formulated in such a way that it promotes, or at least does not degrade, the stability of any enzyme in these compositions.

Preferred systems to be used according to the present inven-tion comprise as a surfactant one or more of the nonionic and/or anionic surfactants described herein.

Polyethylene, polypropylene, and polybutylene oxide conden-sates of alkyl phenols are suitable for use as the nonionic surfactant of the surfactant systems of the present invention, with the polyethylene oxide condensates being preferred. These compounds include the condensation products of alkyl phenols having an alkyl group containing from about 6 to about 14 carbon atoms, preferably from about 8 to about 14 carbon atoms, in either a straight chain or branched-chain configuration with the alkylene oxide. In a preferred embodiment, the ethylene oxide is present in an amount equal to from about 2 to about 25 moles, more preferably from about 3 to about 15 moles, of ethylene oxide per mole of alkyl phenol. Commercially available nonionic surfactants of this type include Igepal™ CO-630, marketed by the GAF Corporation; and Triton™ X-45, X-114, X-100 and X-102, all marketed by the Rohm & Haas Company. These surfactants are commonly referred to as alkylphenol alkoxylates (e.g., alkyl phenol ethoxylates).

The condensation products of primary and secondary aliphatic alcohols with about 1 to about 25 moles of ethylene oxide are suitable for use as the nonionic surfactant of the nonionic surfactant systems of the present invention. The alkyl chain of the aliphatic alcohol can either be straight or branched, primary or secondary, and generally contains from about 8 to about 22 carbon atoms. Preferred are the condensation products of alcohols having an alkyl group containing from about 8 to about 20 carbon atoms, more preferably from about 10 to about 18 carbon atoms, with from about 2 to about 10 moles of ethylene oxide per mole of alcohol. About 2 to about 7 moles of ethylene oxide and most preferably from 2 to 5 moles of ethylene oxide per mole of alcohol are present in said condensation products. Examples of commercially available nonionic surfactants of this type include Tergitol™ 15 S-9 (The condensation product of $C_{11}$–$C_{15}$ linear alcohol with 9 moles ethylene oxide), Tergitol™ 24-L-6 NMW (the condensation product of $C_{12}$–$C_{14}$ primary alcohol with 6 moles ethylene oxide with a narrow molecular weight distribution), both marketed by Union Carbide Corporation; Neodol™ 45–9 (the condensation product of $C_{14}$–$C_{15}$ linear alcohol with 9 moles of ethylene oxide), Neodol™ 23-3 (the condensation product of $C_{12}$–$C_{13}$ linear alcohol with 3.0 moles of ethylene oxide), Neodol™ 45-7 (the condensation product of $C_{14}$–$C_{15}$ linear alcohol with 7 moles of ethylene oxide), Neodol™ 45-5 (the condensation product of $C_{14}$–$C_{15}$ linear alcohol with 5 moles of ethylene oxide) marketed by Shell Chemical Company, Kyro™ EOB (the condensation product of $C_{13}$–$C_{15}$ alcohol with 9 moles ethylene oxide), marketed by The Procter & Gamble Company, and Genapol LA 050 (the condensation product of $C_{12}$–$C_{14}$ alcohol with 5 moles of ethylene oxide) marketed by Hoechst. Preferred range of HLB in these products is from 8–11 and most preferred from 8–10.

Also useful as the nonionic surfactant of the surfactant systems of the present invention are alkylpolysaccharides disclosed in U.S. Pat. No. 4,565,647, having a hydrophobic group containing from about 6 to about 30 carbon atoms, preferably from about 10 to about 16 carbon atoms and a polysaccharide, e.g. a polyglycoside, hydrophilic group containing from about 1.3 to about 10, preferably from about 1.3 to about 3, most preferably from about 1.3 to about 2.7 saccharide units. Any reducing saccharide containing 5 or 6 carbon atoms can be used, e.g., glucose, galactose and galactosyl moieties can be substituted for the glucosyl moieties (optionally the hydrophobic group is attached at the 2-, 3-, 4-, etc. positions thus giving a glucose or galactose as opposed to a glucoside or galactoside). The intersaccharide bonds can be, e.g., between the one position of the additional saccharide units and the 2-, 3-, 4-, and/or 6-positions on the preceding saccharide units.

The preferred alkylpolyglycosides have the formula

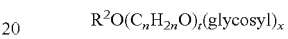

$R^2O(C_nH_{2n}O)_t(glycosyl)_x$ wherein $R^2$ is selected from the group consisting of alkyl, alkylphenyl, hydroxyalkyl, hydroxyalkylphenyl, and mixtures thereof in which the alkyl groups contain from about 10 to about 18, preferably from about 12 to about 14, carbon atoms; n is 2 or 3, preferably 2; t is from 0 to about 10, preferably 0; and x is from about 1.3 to about 10, preferably from about 1.3 to about 3, most preferably from about 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4-, and/or 6-position, preferably predominantly the 2-position.

The condensation products of ethylene oxide with a hydrophobic base formed by the condensation of propylene oxide with propylene glycol are also suitable for use as the additional nonionic surfactant systems of the present invention. The hydrophobic portion of these compounds will preferably have a molecular weight from about 1500 to about 1800 and will exhibit water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to about 40 moles of ethylene oxide. Examples of compounds of this type include certain of the commercially available Pluronic™ surfactants, marketed by BASF.

Also suitable for use as the nonionic surfactant of the nonionic surfactant system of the present invention, are the condensation products of ethylene oxide with the product resulting from the reaction of propylene oxide and ethylenediamine. The hydrophobic moiety of these products consists of the reaction product of ethylenediamine and excess propylene oxide, and generally has a molecular weight of from about 2500 to about 3000. This hydrophobic moiety is condensed with ethylene oxide to the extent that the condensation product contains from about 40% to about 80% by weight of polyoxyethylene and has a molecular weight of from about 5,000 to about 11,000. Examples of this type of nonionic surfactant include certain of the commercially available Tetronic™ compounds, marketed by BASF.

Preferred for use as the nonionic surfactant of the surfactant systems of the present invention are polyethylene oxide condensates of alkyl phenols, condensation products of primary and secondary aliphatic alcohols with from about 1 to about 25 moles of ethyleneoxide, alkylpolysaccharides, and mixtures hereof. Most preferred are $C_8$–$C_{14}$ alkyl phenol ethoxylates having from 3 to 15 ethoxy groups and $C_8$–$C_{18}$ alcohol ethoxylates (preferably $C_{10}$ avg.) having from 2 to 10 ethoxy groups, and mixtures thereof.

Highly preferred nonionic surfactants are polyhydroxy fatty acid amide surfactants of the formula

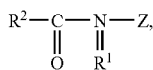

wherein $R^1$ is H, or $R^1$ is $C_{1-4}$ hydrocarbyl, 2-hydroxyethyl, 2-hydroxypropyl or a mixture thereof, $R^2$ is $C_{5-31}$ hydrocarbyl, and Z is a polyhydroxyhydrocarbyl having a linear hydrocarbyl chain with at least 3 hydroxyls directly connected to the chain, or an alkoxylated derivative thereof. Preferably, $R^1$ is methyl, $R^2$ is straight $C_{11-15}$ alkyl or $C_{16-18}$ alkyl or alkenyl chain such as coconut alkyl or mixtures thereof, and Z is derived from a reducing sugar such as glucose, fructose, maltose or lactose, in a reductive amination reaction.

Highly preferred anionic surfactants include alkyl alkoxylated sulfate surfactants. Examples hereof are water soluble salts or acids of the formula $RO(A)_mSO3M$ wherein R is an unsubstituted $C_{10}$–$C_{24}$ alkyl or hydroxyalkyl group having a $C_{10}$–$C_{24}$ alkyl component, preferably a $C_{12}$–$C_{20}$ alkyl or hydro-xyalkyl, more preferably $C_{12}$–$C_{18}$ alkyl or hydroxyalkyl, A is an ethoxy or propoxy unit, m is greater than zero, typically between about 0.5 and about 6, more preferably between about 0.5 and about 3, and M is H or a cation which can be, for example, a metal cation (e.g., sodium, potassium, lithium, calcium, magnesium, etc.), ammonium or substituted-ammonium cation. Alkyl ethoxylated sulfates as well as alkyl propoxylated sulfates are contemplated herein. Specific examples of substituted ammonium cations include methyl-, dimethyl, trimethyl-ammonium cations and quaternary ammonium cations such as tetramethyl-ammonium and dimethyl piperdinium cations and those derived from alkylamines such as ethylamine, diethylamine, triethylamine, mixtures thereof, and the like. Exemplary surfactants are $C_{12}$–$C_{18}$ alkyl polyethoxylate (1.0) sulfate ($C_{12–C18}$E(1.0) M), $C_{12}$–$C_{18}$ alkyl polyethoxylate (2.25) sulfate ($C_{12}$–$C_{18}$ (2.25)M, and $C_{12}$–$C_{18}$ alkyl polyethoxylate (3.0) sulfate ($C_{12}$–$C_{18}$E(3.0)M), and $C_{12}$–$C_{18}$ alkyl polyethoxylate (4.0) sulfate ($C_{12}$–$C_{18}$E(4.0)M), wherein M is conveniently selected from sodium and potassium.

Suitable anionic surfactants to be used are alkyl ester sulfonate surfactants including linear esters of $C_8$–$C_{20}$ carboxylic acids (i.e., fatty acids) which are sulfonated with gaseous $SO_3$ according to "The Journal of the American Oil Chemists Society", 52 (1975), pp. 323–329. Suitable starting materials would include natural fatty substances as derived from tallow, palm oil, etc.

The preferred alkyl ester sulfonate surfactant, especially for laundry applications, comprise alkyl ester sulfonate surfactants of the structural formula:

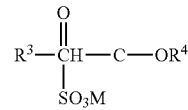

wherein $R^3$ is a $C_8$–$C_{20}$ hydrocarbyl, preferably an alkyl, or combination thereof, $R^4$ is a $C_1$–$C_6$ hydrocarbyl, preferably an alkyl, or combination thereof, and M is a cation which forms a water soluble salt with the alkyl ester sulfonate. Suitable salt-forming cations include metals such as sodium, potassium, and lithium, and substituted or unsubstituted ammonium cations, such as monoethanolamine, diethonolamine, and triethanolamine. Preferably, $R^3$ is $C_{10}$–$C_{16}$ alkyl, and $R^4$ is methyl, ethyl or isopropyl. Especially preferred are the methyl ester sulfonates wherein $R^3$ is $C_{10}$–$C_{16}$ alkyl.

Other suitable anionic surfactants include the alkyl sulfate surfactants which are water soluble salts or acids of the formula $ROSO_3M$ wherein R preferably is a $C_{10}$–$C_{24}$ hydrocarbyl, preferably an alkyl or hydroxyalkyl having a $C_{10}$–$C_{20}$ alkyl component, more preferably a $C_{12}$–$C_{18}$ alkyl or hydroxyalkyl, and M is H or a cation, e.g., an alkali metal cation (e.g. sodium, potassium, lithium), or ammonium or substituted ammonium (e.g. methyl-, dimethyl-, and trimethyl ammonium cations and quaternary ammonium cations such as tetramethyl-ammonium and dimethyl piperdinium cations and quaternary ammonium cations derived from alkylamines such as ethylamine, diethylamine, triethylamine, and mixtures thereof, and the like). Typically, alkyl chains of $C_{12}$–$C_{16}$ are preferred for lower wash temperatures (e.g. below about 50 C.) and $C_{16}$–$C_{18}$ alkyl chains are preferred for higher wash temperatures (e.g. above about 50 C.).

Other anionic surfactants useful for detersive purposes can also be included in the laundry detergent compositions of the present invention. Theses can include salts (including, for example, sodium, potassium, ammonium, and substituted ammonium salts such as mono- di- and triethanolamine salts) of soap, $C_8$–$C_{22}$ primary or secondary alkanesulfonates, $C_8$–$C_{24}$ olefinsulfonates, sulfonated polycarboxylic acids prepared by sulfonation of the pyrolyzed product of alkaline earth metal citrates, e.g., as described in British patent specification No. 1,082,179, $C_8$–$C_{24}$ alkylpolyglycolethersulfates (containing up to 10 moles of ethylene oxide); alkyl glycerol sulfonates, fatty acyl glycerol sulfonates, fatty oleyl glycerol sulfates, alkyl phenol ethylene oxide ether sulfates, paraffin sulfonates, alkyl phosphates, isethionates such as the acyl isethionates, N-acyl taurates, alkyl succinamates and sulfosuccinates, monoesters of sulfosuccinates (especially saturated and unsaturated $C_{12}$–$C_{18}$ monoesters) and diesters of sulfosuccinates (especially saturated and unsaturated $C_6$–$C_{12}$ diesters), acyl sarcosinates, sulfates of alkylpolysaccharides such as the sulfates of alkylpolyglucoside (the nonionic nonsulfated compounds being described below), branched primary alkyl sulfates, and alkyl polyethoxy carboxylates such as those of the formula $RO(CH_2CH_2O)_k$—$CH_2COO$—M+ wherein R is a $C_8$–$C_{22}$ alkyl, k is an integer from 1 to 10, and M is a soluble salt forming cation. Resin acids and hydrogenated resin acids are also suitable, such as rosin, hydrogenated rosin, and resin acids and hydrogenated resin acids present in or derived from tall oil.

Alkylbenzene sulfonates are highly preferred. Especially preferred are linear (straight-chain) alkyl benzene sulfonates (LAS) wherein the alkyl group preferably contains from 10 to 18 carbon atoms.

Further examples are described in "Surface Active Agents and Detergents" (Vol. I and II by Schwartz, Perrry and Berch). A variety of such surfactants are also generally disclosed in U.S. Pat. No. 3,929,678, (Column 23, line 58 through Column 29, line 23, herein incorporated by reference).

When included therein, the laundry detergent compositions of the present invention typically comprise from about 1% to about 40%, preferably from about 3% to about 20% by weight of such anionic surfactants.

The laundry detergent compositions of the present invention may also contain cationic, ampholytic, zwitterionic, and semi-polar surfactants, as well as the nonionic and/or anionic surfactants other than those already described herein.

Cationic detersive surfactants suitable for use in the laundry detergent compositions of the present invention are those having one long-chain hydrocarbyl group. Examples of such cationic surfactants include the ammonium surfactants such as alkyltrimethylammonium halogenides, and those surfactants having the formula:

$$[R^2(OR^3)_y][R^4(OR^3)_y]_2R^5N+X-$$

wherein $R^2$ is an alkyl or alkyl benzyl group having from about 8 to about 18 carbon atoms in the alkyl chain, each $R^3$ is selected form the group consisting of $-CH_2CH_2-$, $-CH_2CH(CH_3)-$, $-CH_2CH(CH_2OH)-$, $-CH_2CH_2CH_2-$, and mixtures thereof; each $R^4$ is selected from the group consisting of $C_1-C_4$ alkyl, $C_1-C_4$ hydroxyalkyl, benzyl ring structures formed by joining the two $R^4$ groups, $-CH_2CHOHCHOHCOR^6CHOHCH_2OH$, wherein $R^6$ is any hexose or hexose polymer having a molecular weight less than about 1000, and hydrogen when y is not 0; $R^5$ is the same as $R^4$ or is an alkyl chain, wherein the total number of carbon atoms or $R^2$ plus $R^5$ is not more than about 18; each y is from 0 to about 10,and the sum of the y values is from 0 to about 15; and X is any compatible anion.

Highly preferred cationic surfactants are the water soluble quaternary ammonium compounds useful in the present composition having the formula:

$$R_1R_2R_3R_4N^+X^- \quad (i)$$

wherein $R_1$ is $C_8-C_{16}$ alkyl, each of $R_2$, $R_3$ and $R_4$ is independently $C_1-C_4$ alkyl, $C_1-C_4$ hydroxy alkyl, benzyl, and $-(C_2H_{40})_xH$ where x has a value from 2 to 5, and X is an anion. Not more than one of $R_2$, $R_3$ or $R_4$ should be benzyl.

The preferred alkyl chain length for $R_1$ is $C_{12}-C_{15}$, particularly where the alkyl group is a mixture of chain lengths derived from coconut or palm kernel fat or is derived synthetically by olefin build up or OXO alcohols synthesis.

Preferred groups for $R_2R_3$ and $R_4$ are methyl and hydroxyethyl groups and the anion X may be selected from halide, methosulphate, acetate and phosphate ions.

Examples of suitable quaternary ammonium compounds of formulae (i) for use herein are:

coconut trimethyl ammonium chloride or bromide;
coconut methyl dihydroxyethyl ammonium chloride or bromide;
decyl triethyl ammonium chloride;
decyl dimethyl hydroxyethyl ammonium chloride or bromide;
$C_{12-15}$ dimethyl hydroxyethyl ammonium chloride or bromide;
coconut dimethyl hydroxyethyl ammonium chloride or bromide;
myristyl trimethyl ammonium methyl sulphate;
lauryl dimethyl benzyl ammonium chloride or bromide;
lauryl dimethyl (ethenoxy)$_4$ ammonium chloride or bromide;
choline esters (compounds of formula (i) wherein $R_1$ is

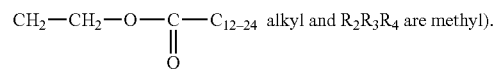

di-alkyl imidazolines [compounds of formula (i)].

Other cationic surfactants useful herein are also described in U.S. Pat. No. 4,228,044 and in EP 000 224.

When included therein, the laundry detergent compositions of the present invention typically comprise from 0.2% to about 25%, preferably from about 1% to about 8% by weight of such cationic surfactants.

Ampholytic surfactants are also suitable for use in the laundry detergent compositions of the present invention. These surfactants can be broadly described as aliphatic derivatives of secondary or tertiary amines, or aliphatic derivatives of heterocyclic secondary and tertiary amines in which the aliphatic radical can be straight- or branched-chain. One of the aliphatic substituents contains at least about 8 carbon atoms, typically from about 8 to about 18 carbon atoms, and at least one contains an anionic water-solubilizing group, e.g. carboxy, sulfonate, sulfate. See U.S. Pat. No. 3,929,678 (column 19, lines 18–35) for examples of ampholytic surfactants.

When included therein, the laundry detergent compositions of the present invention typically comprise from 0.2% to about 15%, preferably from about 1% to about 10% by weight of such ampholytic surfactants.

Zwitterionic surfactants are also suitable for use in laundry detergent compositions. These surfactants can be broadly described as derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678 (column 19, line 38 through column 22, line 48) for examples of zwitterionic surfactants.

When included therein, the laundry detergent compositions of the present invention typically comprise from 0.2% to about 15%, preferably from about 1% to about 10% by weight of such zwitterionic surfactants.

Semi-polar nonionic surfactants are a special category of nonionic surfactants which include water-soluble amine oxides containing one alkyl moiety of from about 10 to about 18 carbon atoms and 2 moieties selected from the group consisting of alkyl groups and hydroxyalkyl groups containing from about 1 to about 3 carbon atoms; water-soluble phosphine oxides containing one alkyl moiety of from about 10 to about 18 carbon atoms and 2 moieties selected from the group consisting of alkyl groups and hydroxyalkyl groups containing from about 1 to about 3 carbon atoms; and water-soluble sulfoxides containing one alkyl moiety from about 10 to about 18 carbon atoms and a moiety selected from the group consisting of alkyl and hydroxyalkyl moieties of from about 1 to about 3 carbon atoms.

Semi-polar nonionic detergent surfactants include the amine oxide surfactants having the formula:

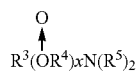

wherein $R^3$ is an alkyl, hydroxyalkyl, or alkyl phenyl group or mixtures thereof containing from about 8 to about 22 carbon atoms; $R^4$ is an alkylene or hydroxyalkylene group containing from about 2 to about 3 carbon atoms or mixtures thereof; x is from 0 to about 3: and each $R^5$ is an alkyl or hydroxyalkyl group containing from about 1 to about 3 carbon atoms or a polyethylene oxide group containing from about 1 to about 3 ethylene oxide groups. The $R^5$ groups can be attached to each other, e.g., through an oxygen or nitrogen atom, to form a ring structure.

These amine oxide surfactants in particular include $C_{10}$–$C_{18}$ alkyl dimethyl amine oxides and $C_8$–$C_{12}$ alkoxy ethyl dihydroxy ethyl amine oxides.

When included therein, the laundry detergent compositions of the present invention typically comprise from 0.2% to about 15%, preferably from about 1% to about 10% by weight of such semi-polar nonionic surfactants.

Builder System

The compositions according to the present invention may further comprise a builder system. Any conventional builder system is suitable for use herein including aluminosilicate materials, silicates, polycarboxylates and fatty acids, materials such as ethylenediamine tetraacetate, metal ion sequestrants such as aminopolyphosphonates, particularly ethylenediamine tetramethylene phosphonic acid and diethylene triamine pentamethylenephosphonic acid. Though less preferred for obvious environmental reasons, phosphate builders can also be used herein.

Suitable builders can be an inorganic ion exchange material, commonly an inorganic hydrated aluminosilicate material, more particularly a hydrated synthetic zeolite such as hydrated zeolite A, X, B, HS or MAP.

Another suitable inorganic builder material is layered silicate, e.g. SKS-6 (Hoechst). SKS-6 is a crystalline layered silicate consisting of sodium silicate ($Na_2Si_2O_5$).

Suitable polycarboxylates containing one carboxy group include lactic acid, glycolic acid and ether derivatives thereof as disclosed in Belgian Patent Nos. 831,368, 821,369 and 821,370. Polycarboxylates containing two carboxy groups include the water-soluble salts of succinic acid, malonic acid, (ethylenedioxy) diacetic acid, maleic acid, diglycollic acid, tartaric acid, tartronic acid and fumaric acid, as well as the ether carboxylates described in German Offenle-enschrift 2,446,686, and 2,446,487, U.S. Pat. No. 3,935,257 and the sulfinyl carboxylates described in Belgian Patent No. 840,623. Polycarboxylates containing three carboxy groups include, in particular, water-soluble citrates, aconitrates and citraconates as well as succinate derivatives such as the carboxymethyloxysuccinates described in British Patent No. 1,379,241, lactoxysuccinates described in Netherlands Application 7205873, and the oxypolycarboxylate materials such as 2-oxa-1,1,3-propane tricarboxylates described in British Patent No. 1,387,447.

Polycarboxylates containing four carboxy groups include oxydisuccinates disclosed in British Patent No.1,261,829,1, 1,2,2,-ethane tetracarboxylates, 1,1,3,3-propane tetracarboxylates containing sulfo substituents include the sulfosuccinate derivatives disclosed in British Patent Nos. 1,398, 421 and 1,398,422 and in U.S. Pat. No. 3,936,448, and the sulfonated pyrolysed citrates described in British Patent No. 1,082,179, while polycarboxylates containing phosphone substituents are disclosed in British Patent No. 1,439,000.

Alicyclic and heterocyclic polycarboxylates include cyclopentane-cis,cis-cis-tetracarboxylates, cyclopentadienide pentacarboxylates, 2,3,4,5-tetrahydrofuran-cis, cis, cis-tetracarboxylates, 2,5-tetrahydro-furan-cis, discarboxylates, 2,2,5,5,-tetrahydrofuran-tetracarboxylates, 1,2,3,4,5,6-hexane-hexacarboxylates and carboxymethyl derivatives of polyhydric alcohols such as sorbitol, mannitol and xylitol. Aromatic polycarboxylates include mellitic acid, pyromellitic acid and the phthalic acid derivatives disclosed in British Patent No. 1,425,343.

Of the above, the preferred polycarboxylates are hydroxycarboxylates containing up to three carboxy groups per molecule, more particularly citrates.

Preferred builder systems for use in the present compositions include a mixture of a water-insoluble aluminosilicate builder such as zeolite A or of a layered silicate (SKS-6), and a water-soluble carboxylate chelating agent such as citric acid.

A suitable chelant for inclusion in the detergent compositions in accordance with the invention is ethylenediamine-N,N'-disuccinic acid (EDDS) or the alkali metal, alkaline earth metal, ammonium, or substituted ammonium salts thereof, or mixtures thereof. Preferred EDDS compounds are the free acid form and the sodium or magnesium salt thereof. Examples of such preferred sodium salts of EDDS include $Na_2EDDS$ and $Na_4EDDS$. Examples of such preferred magnesium salts of EDDS include MgEDDS and $Mg_2EDDS$. The magnesium salts are the most preferred for inclusion in compositions in accordance with the invention.

Preferred builder systems include a mixture of a water-insoluble aluminosilicate builder such as zeolite A, and a water soluble carboxylate chelating agent such as citric acid.

Other builder materials that can form part of the builder system for use in granular compositions include inorganic materials such as alkali metal carbonates, bicarbonates, silicates, and organic materials such as the organic phosphonates, amino polyalkylene phosphonates and amino polycarboxylates.

Other suitable water-soluble organic salts are the homo- or co-polymeric acids or their salts, in which the polycarboxylic acid comprises at least two carboxyl radicals separated form each other by not more than two carbon atoms.

Polymers of this type are disclosed in GB-A-1,596,756. Examples of such salts are polyacrylates of MW 2000–5000 and their copolymers with maleic anhydride, such copolymers having a molecular weight of from 20,000 to 70,000, especially about 40,000.

Detergency builder salts are normally included in amounts of from 5% to 80% by weight of the composition. Preferred levels of builder for liquid detergents are from 5% to 30%.

Enzymes

Preferred detergent compositions, in addition to the enzyme preparation of the invention, comprise other enzyme(s) which provides cleaning performance and/or fabric care benefits.

Such enzymes include proteases, lipases, cutinases, amylases, cellulases, peroxidases, oxidases (e.g. laccases).

Proteases:

Any protease suitable for use in alkaline solutions can be used. Suitable proteases include those of animal, vegetable or microbial origin. Microbial origin is preferred. Chemically or genetically modified mutants are included. The protease may be a serine protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the *Fusarium* protease described in WO 89/06270.

Preferred commercially available protease enzymes include those sold under the trade names ALCALASE, SAVINASE, PRIMASE, DURAZYM, and ESPERASE by Novo Nordisk A/S (Denmark), those sold under the tradename MAXATASE, MAXACAL, MAXAPEM, PROPERASE, PURAFECT and PURAFECT OXP by Genencor International, and those sold under the tradename OPTICLEAN and OPTIMASE by Solvay Enzymes. Protease enzymes may be incorporated into the compositions in accordance with the invention at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Lipases:

Any lipase suitable for use in alkaline solutions can be used. Suitable lipases include those of bacterial or fungal origin. Chemically or genetically modified mutants are included.

Examples of useful lipases include a *Humicola lanuginosa* lipase, e.g., as described in EP 258 068 and EP 305 216, a *Rhizomucor miehei* lipase, e.g., as described in EP 238 023, a *Candida* lipase, such as a *C. antarctica* lipase, e.g., the *C. antarctica* lipase A or B described in EP 214 761, a *Pseudomonas* lipase such as a *P. alcaligenes* and *P. pseudoalcaligenes* lipase, e.g., as described in EP 218 272, a *P. cepacia* lipase, e.g., as described in EP 331 376, a *P. stutzeri* lipase, e.g., as disclosed in GB 1,372,034, a *P. fluorescens* lipase, a *Bacillus* lipase, e.g., a *B. subtilis* lipase (Dartois et al., (1993), Biochemica et Biophysica acta 1131, 253–260), a *B. stearothermophilus* lipase (JP 64/744992) and a *B. pumilus* lipase (WO 91/16422).

Furthermore, a number of cloned lipases may be useful, including the *Penicillium camembertii* lipase described by Yamaguchi et al., (1991), Gene 103, 61–67), the *Geotricum candidum* lipase (Schimada, Y. et al., (1989), J. Biochem., 106, 383–388), and various *Rhizopus* lipases such as a *R. delemar* lipase (Hass, M. J et al., (1991), Gene 109, 117–113), a *R. niveus* lipase (Kugimiya et al., (1992), Biosci. Biotech. Biochem. 56, 716–719) and a *R. oryzae* lipase.

Other types of lipolytic enzymes such as cutinases may also be useful, e.g., a cutinase derived from *Pseudomonas mendocina* as described in WO 88/09367, or a cutinase derived from *Fusarium solani pisi* (e.g. described in WO 90/09446).

Especially suitable lipases are lipases such as M1 Lipase™, Luma fast™ and Lipomax™ (Genencor), Lipolase™ and Lipolase Ultra™ (Novo Nordisk A/S), and Lipase P "Amano" (Amano Pharmaceutical Co. Ltd.).

The lipases are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Amylases:

Any amylase (alpha and/or beta) suitable for use in alkaline solutions can be used. Suitable amylases include those of bacterial or fungal origin. Chemically or genetically modified mutants are included. Amylases include, for example, alpha-amylases obtained from a special strain of *B. licheniformis*, described in more detail in GB 1,296,839. Commercially available amylases are Duramyl™, Termamyl™, Fungamyl™ and BAN™ (available from Novo Nordisk A/S) and Rapidase™ and Maxamyl P™ (available from Genencor).

The amylases are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Cellulases:

Any cellulase suitable for use in alkaline solutions can be used. Suitable cellulases include those of bacterial or fungal origin. Chemically or genetically modified mutants are included. Suitable cellulases are disclosed in U.S. Pat. No. 4,435,307, which discloses fungal cellulases produced from *Humicola insolens*. Especially suitable cellulases are the cellulases having colour care benefits. Examples of such cellulases are cellulases described in European patent application No. 0 495 257.

Commercially available cellulases include Celluzyme produced by a strain of *Humicola insolens*, (Novo Nordisk A/S), and KAC-500(B) (Kao Corporation).

Cellulases are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Peroxidases/Oxidases:

Peroxidase enzymes are used in combination with hydrogen peroxide or a source thereof (e.g. a percarbonate, perborate or persulfate). Oxidase enzymes are used in combination with oxygen. Both types of enzymes are used for "solution bleaching", i.e. to prevent transfer of a textile dye from a dyed fabric to another fabric when said fabrics are washed together in a wash liquor, preferably together with an enhancing agent as described in e.g. WO 94/12621 and WO 95/01426. Suitable peroxidases/oxidases include those of plant, bacterial or fungal origin. Chemically or genetically modified mutants are included.

Peroxidase and/or oxidase enzymes are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Mixtures of the above mentioned enzymes are encompassed herein, in particular a mixture of a protease, an amylase, a lipase and/or a cellulase.

The enzyme of the invention, or any other enzyme incorporated in the detergent composition, is normally incorporated in the detergent composition at a level from 0.00001% to 2% of enzyme protein by weight of the composition, preferably at a level from 0.0001% to 1% of enzyme protein by weight of the composition, more preferably at a level from 0.001% to 0.5% of enzyme protein by weight of the composition, even more preferably at a level from 0.01% to 0.2% of enzyme protein by weight of the composition.

Bleaching Agents:

Additional optional detergent ingredients that can be included in the detergent compositions of the present invention include bleaching agents such as PB1, PB4 and percarbonate with a particle size of 400–800 microns. These bleaching agent components can include one or more oxygen bleaching agents and, depending upon the bleaching agent chosen, one or more bleach activators. When present oxygen bleaching compounds will typically be present at levels of from about 1% to about 25%. In general, bleaching compounds are optional added components in non-liquid formulations, e.g. granular detergents.

The bleaching agent component for use herein can be any of the bleaching agents useful for detergent compositions including oxygen bleaches as well as others known in the art.

The bleaching agent suitable for the present invention can be an activated or non-activated bleaching agent.

One category of oxygen bleaching agent that can be used encompasses percarboxylic acid bleaching agents and salts thereof. Suitable examples of this class of agents include magnesium monoperoxyphthalate hexahydrate, the magnesium salt of meta-chloro perbenzoic acid, 4-nonylamino-4-oxoperoxybutyric acid and diperoxydodecanedioic acid. Such bleaching agents are disclosed in U.S. Pat. No. 4,483,781, U.S. Pat. No. 740,446, EP 0 133 354 and U.S. Pat. No. 4,412,934. Highly preferred bleaching agents also include 6-nonylamino-6-oxoperoxycaproic acid as described in U.S. Pat. No. 4,634,551.

Another category of bleaching agents that can be used encompasses the halogen bleaching agents. Examples of hypohalite bleaching agents, for example, include trichloro isocyanuric acid and the sodium and potassium dichloroisocyanurates and N-chloro and N-bromo alkane sulphonamides. Such materials are normally added at 0.5–10% by weight of the finished product, preferably 1–5% by weight.

The hydrogen peroxide releasing agents can be used in combination with bleach activators such as tetra-acetylethylenediamine (TAED), nonanoyloxybenzenesulfonate (NOBS, described in U.S. Pat. No. 4,412,934), 3,5-trimethyl-hexsanoloxybenzenesulfonate (ISONOBS, described in EP 120 591) or pentaacetylglucose (PAG), which are perhydrolyzed to form a peracid as the active bleaching species, leading to improved bleaching effect. In addition, very suitable are the bleach activators C8(6-octanamido-caproyl) oxybenzene-sulfonate, C9(6-nonanamido caproyl) oxybenzenesulfonate and C10 (6-decanamido caproyl) oxy-benzenesulfonate or mixtures thereof. Also suitable activators are acylated citrate esters such as disclosed in European Patent Application No. 91870207.7.

Useful bleaching agents, including peroxyacids and bleaching systems comprising bleach activators and peroxygen bleaching compounds for use in cleaning compositions according to the invention are described in application U.S. Ser. No. 08/136,626.

The hydrogen peroxide may also be present by adding an enzymatic system (i.e. an enzyme and a substrate therefore) which is capable of generation of hydrogen peroxide at the beginning or during the washing and/or rinsing process. Such enzymatic systems are disclosed in European Patent Application EP 0 537 381.

Bleaching agents other than oxygen bleaching agents are also known in the art and can be utilized herein. One type of non-oxygen bleaching agent of particular interest includes photoactivated bleaching agents such as the sulfonated zinc and/or aluminium phthalocyanines. These materials can be deposited upon the substrate during the washing process. Upon irradiation with light, in the presence of oxygen, such as by hanging clothes out to dry in the daylight, the sulfonated zinc phthalocyanine is activated and, consequently, the substrate is bleached. Preferred zinc phthalocyanine and a photoactivated bleaching process are described in U.S. Pat. No. 4,033,718. Typically, detergent composition will contain about 0.025% to about 1.25%, by weight, of sulfonated zinc phthalocyanine.

Bleaching agents may also comprise a manganese catalyst. The manganese catalyst may, e.g., be one of the compounds described in "Efficient manganese catalysts for low-temperature bleaching", *Nature* 369, 1994, pp. 637–639.

Suds Suppressors:

Another optional ingredient is a suds suppressor, exemplified by silicones, and silica-silicone mixtures. Silicones can generally be represented by alkylated polysiloxane materials, while silica is normally used in finely divided forms exemplified by silica aerogels and xerogels and hydrophobic silicas of various types. Theses materials can be incorporated as particulates, in which the suds suppressor is advantageously releasably incorporated in a water-soluble or waterdispersible, substantially non surface-active detergent impermeable carrier. Alternatively the suds suppressor can be dissolved or dispersed in a liquid carrier and applied by spraying on to one or more of the other components.

A preferred silicone suds controlling agent is disclosed in U.S. Pat. No. 3,933,672. Other particularly useful suds suppressors are the self-emulsifying silicone suds suppressors, described in German Patent Application DTOS 2,646,126. An example of such a compound is DC-544, commercially available form Dow Corning, which is a siloxane-glycol copolymer. Especially preferred suds controlling agent are the suds suppressor system comprising a mixture of silicone oils and 2-alkyl-alkanols. Suitable 2-alkyl-alkanols are 2-butyl-octanol which are commercially available under the trade name Isofol 12 R.

Such suds suppressor system are described in European Patent Application EP 0 593 841.

Especially preferred silicone suds controlling agents are described in European Patent Application No. 92201649.8. Said compositions can comprise a silicone/silica mixture in combination with fumed nonporous silica such as Aerosil$^R$.

The suds suppressors described above are normally employed at levels of from 0.001% to 2% by weight of the composition, preferably from 0.01% to 1% by weight.

Other Components:

Other components used in detergent compositions may be employed such as soil-suspending agents, soil-releasing agents, optical brighteners, abrasives, bactericides, tarnish inhibitors, coloring agents, and/or encapsulated or nonencapsulated perfumes.

Especially suitable encapsulating materials are water soluble capsules which consist of a matrix of polysaccharide and polyhydroxy compounds such as described in GB 1,464,616.

Other suitable water soluble encapsulating materials comprise dextrins derived from ungelatinized starch acid esters of substituted dicarboxylic acids such as described in U.S. Pat. No. 3,455,838. These acid-ester dextrins are, preferably, prepared from such starches as waxy maize, waxy sorghum, sago, tapioca and potato. Suitable examples of said encapsulation materials include N-Lok manufactured by National Starch. The N-Lok encapsulating material consists of a modified maize starch and glucose. The starch is modified by adding monofunctional substituted groups such as octenyl succinic acid anhydride.

Antiredeposition and soil suspension agents suitable herein include cellulose derivatives such as methylcellulose, carboxymethylcellulose and hydroxyethylcellulose, and homo- or co-polymeric polycarboxylic acids or their salts. Polymers of this type include the polyacrylates and maleic anhydride-acrylic acid copolymers previously mentioned as builders, as well as copolymers of maleic anhydride with ethylene, methylvinyl ether or methacrylic acid, the maleic anhydride constituting at least 20 mole percent of the copolymer. These materials are normally used at levels of from 0.5% to 10% by weight, more preferably form 0.75% to 8%, most preferably from 1% to 6% by weight of the composition.

Preferred optical brighteners are anionic in character, examples of which are disodium 4,4'-bis-(2-diethanolamino-4-anilino -s-triazin-6-ylamino)stilbene-2:2'disulphonate, disodium 4,4'-bis-(2-morpholino-4-anilino-s-triazin-6-ylamino-stilbene-2:2'-disulphonate, disodium 4,4'-bis-(2,4-dianilino-s-triazin-6-ylamino)stilbene-2:2'-disulphonate, monosodium 4',4"-bis-(2,4-dianilino-s-tri-azin-6-ylamino) stilbene-2-sulphonate, disodium 4,4'-bis-(2-anilino-4-(N-methyl-N-2-hydroxyethylamino)-s-triazin-6-ylamino)stilbene-2,2'-disulphonate, di-sodium 4,4'-bis-(4-phenyl-2,1,3-triazol-2-yl)-stilbene-2,2'disulphonate, di-sodium 4,4'-bis(2-anilino-4-(1-methyl-2-hydroxyethylamino)-s-triazin-6-ylami-no)stilbene-2,2'disulphonate, sodium 2(stilbyl-4"-(naphtho-1', 2':4,5)-1,2,3-triazole-2"-sulphonate and 4,4'-bis (2-sulphostyryl)biphenyl.

Other useful polymeric materials are the polyethylene glycols, particularly those of molecular weight 1000–10000, more particularly 2000 to 8000 and most preferably about 4000. These are used at levels of from 0.20% to 5% more preferably from 0.25% to 2.5% by weight. These polymers and the previously mentioned homo- or co-polymeric polycarboxylate salts are valuable for improving whiteness maintenance, fabric ash deposition, and cleaning performance on clay, proteinaceous and oxidizable soils in the presence of transition metal impurities.

Soil release agents useful in compositions of the present invention are conventionally copolymers or terpolymers of terephthalic acid with ethylene glycol and/or propylene glycol units in various arrangements. Examples of such polymers are disclosed in U.S. Pat. No. 4,116,885 and 4,711,730 and EP 0 272 033. A particular preferred polymer in accordance with EP 0 272 033 has the formula:

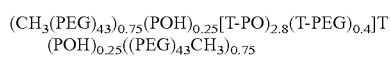

where PEG is —(OC$_2$H$_4$)0-, PO is (OC$_3$H$_6$O) and T is (POOC$_6$H$_4$CO).

Also very useful are modified polyesters as random copolymers of dimethyl terephthalate, dimethyl sulfoisophthalate, ethylene glycol and 1,2-propanediol, the end groups consisting primarily of sulphobenzoate and secondarily of mono esters of ethylene glycol and/or 1,2-propanediol. The target is to obtain a polymer capped at both end by sulphobenzoate groups, "primarily", in the present context most of said copolymers herein will be endcapped by sulphobenzoate groups. However, some copolymers will be less than fully capped, and therefore their end groups may consist of monoester of ethylene glycol and/or 1,2-propanediol, thereof consist "secondarily" of such species.

The selected polyesters herein contain about 46% by weight of dimethyl terephthalic acid, about 16% by weight of 1,2-propanediol, about 10% by weight ethylene glycol, about 13% by weight of dimethyl sulfobenzoic acid and about 15% by weight of sulfoisophthalic acid, and have a molecular weight of about 3.000. The polyesters and their method of preparation are described in detail in EP 311 342.

Softening Agents:

Fabric softening agents can also be incorporated into laundry detergent compositions in accordance with the present invention. These agents may be inorganic or organic in type. Inorganic softening agents are exemplified by the smectite clays disclosed in GB-A-1 400898 and in U.S. Pat. No. 5,019,292. Organic fabric softening agents include the water insoluble tertiary amines as disclosed in GB-A1 514 276 and EP 0 011 340 and their combination with mono C$_{12}$–C$_{14}$ quaternary ammonium salts are disclosed in EP-B-0 026 528 and di-long-chain amides as disclosed in EP 0 242 919. Other useful organic ingredients of fabric softening systems include high molecular weight polyethylene oxide materials as disclosed in EP 0 299 575 and 0 313 146.

Levels of smectite clay are normally in the range from 5% to 15%, more preferably from 8% to 12% by weight, with the material being added as a dry mixed component to the remainder of the formulation. Organic fabric softening agents such as the water-insoluble tertiary amines or dilong chain amide materials are incorporated at levels of from 0.5% to 5% by weight, normally from 1% to 3% by weight whilst the high molecular weight polyethylene oxide materials and the water soluble cationic materials are added at levels of from 0.1% to 2%, normally from 0.15% to 1.5% by weight. These materials are normally added to the spray dried portion of the composition, although in some instances it may be more convenient to add them as a dry mixed particulate, or spray them as molten liquid on to other solid components of the composition.

Polymeric Dye-transfer Inhibiting Agents:

The detergent compositions according to the present invention may also comprise from 0.001% to 10%, preferably from 0.01% to 2%, more preferably form 0.05% to 1% by weight of polymeric dye-transfer inhibiting agents. Said polymeric dye-transfer inhibiting agents are normally incorporated into detergent compositions in order to inhibit the transfer of dyes from colored fabrics onto fabrics washed therewith. These polymers have the ability of complexing or adsorbing the fugitive dyes washed out of dyed fabrics before the dyes have the opportunity to become attached to other articles in the wash.

Especially suitable polymeric dye-transfer inhibiting agents are polyamine N-oxide polymers, copolymers of N-vinyl-pyrrolidone and N-vinylimidazole, polyvinylpyrrolidone polymers, polyvinyloxazolidones and polyvinylimidazoles or mixtures thereof.

Addition of such polymers also enhances the performance of the enzymes according the invention.

The detergent composition according to the invention can be in liquid, paste, gels, bars or granular forms.

Non-dusting granulates may be produced, e.g., as disclosed in U.S. Pat. Nos. 4,106,991 and 4,661,452 (both to Novo Industri A/S) and may optionally be coated by methods known in the art. Examples of waxy coating materials are poly(ethylene oxide) products (polyethyleneglycol, PEG) with mean molecular weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591.

Granular compositions according to the present invention can also be in "compact form", i.e. they may have a relatively higher density than conventional granular detergents, i.e. form 550 to 950 g/l; in such case, the granular detergent compositions according to the present invention will contain a lower amount of "Inorganic filler salt", compared to conventional granular detergents; typical filler salts are alkaline earth metal salts of sulphates and chlorides, typically sodium sulphate; "Compact" detergent typically comprise not more than 10% filler salt. The liquid compositions according to the present invention can also be in "concentrated form", in such case, the liquid detergent compositions according to the present invention will contain a lower amount of water, compared to conventional liquid detergents. Typically, the water content of the concentrated liquid detergent is less than 30%, more preferably less than 20%, most preferably less than 10% by weight of the detergent compositions.

The compositions of the invention may for example, be formulated as hand and machine laundry detergent compositions including laundry additive compositions and compositions suitable for use in the pretreatment of stained fabrics, rinse added fabric softener compositions, and compositions for use in general household hard surface cleaning operations and dishwashing operations.

The following examples are meant to exemplify compositions for the present invention, but are not necessarily meant to limit or otherwise define the scope of the invention.

In the detergent compositions, the abbreviated component identifications have the following meanings:

| LAS: | Sodium linear $C_{12}$ alkyl benzene sulphonate |
| --- | --- |
| TAS: | Sodium tallow alkyl sulphate |
| XYAS: | Sodium $C_{1x}$–$C_{1Y}$ alkyl sulfate |
| SS: | Secondary soap surfactant of formula 2-butyl octanoic acid |
| 25EY: | A $C_{12}$–$C_{15}$ predominantly linear primary alcohol condensed with an average of Y moles of ethylene oxide |
| 45EY: | A $C_{14}$–$C_{15}$ predominantly linear primary alcohol condensed with an average of Y moles of ethylene oxide |
| XYEZS: | $C_{1x}$–$C_{1Y}$ sodium alkyl sulfate condensed with an average of Z moles of ethylene oxide per mole |
| Nonionic: | $C_{13}$–$C_{15}$ mixed ethoxylated/propoxylated fatty alcohol with an average degree of ethoxylation of 3.8 and an average degree of propoxylation of 4.5 sold under the tradename Plurafax LF404 by BASF Gmbh |
| CFAA: | $C_{12}$–$C_{14}$ alkyl N-methyl glucamide |
| TFAA: | $C_{16}$–$C_{18}$ alkyl N-methyl glucamide |
| Silicate: | Amorphous Sodium Silicate ($SiO_2$:$Na_2O$ ratio = 2.0) |
| NaSKS-6: | Crystalline layered silicate of formula delta-$Na_2Si_2O_5$ |
| Carbonate: | Anhydrous sodium carbonate |
| Phosphate: | Sodium tripolyphosphate |
| MA/AA: | Copolymer of 1:4 maleic/acrylic acid, average molecular weight about 80,000 |
| Polyacrylate: | Polyacrylate homopolymer with an average molecular weight of 8,000 sold under the tradename PA30 by BASF Gmbh |
| Zeolite A: | Hydrated Sodium Aluminosilicate of formula $Na_{12}(AlO_2SiO_2)_{12}\cdot 27H_2O$ having a primary particle size in the range from 1 to 10 micrometers |
| Citrate: | Tri-sodium citrate dihydrate |
| Citric: | Citric Acid |
| Perborate: | Anhydrous sodium perborate monohydrate bleach, empirical formula $NaBO_2\cdot H_2O_2$ |
| PB4: | Anhydrous sodium perborate tetrahydrate |
| Percarbonate: | Anhydrous sodium percarbonate bleach of empirical formula $2Na_2CP_3\cdot 3H_2O_2$ |
| TAED: | Tetraacetyl ethylene diamine |
| CMC: | Sodium carboxymethyl cellulose |
| DETPMP: | Diethylene triamine penta (methylene phosphonic acid), marketed by Monsanto under the Tradename Dequest 2060 |
| PVP: | Polyvinylpyrrolidone polymer |
| EDDS: | Ethylenediamine-N,N'-disuccinic acid, [S,S] isomer in the form of the sodium salt |
| Suds | 25% paraffin wax Mpt 50° C., 17% hydrophobic silica, 58% |
| Suppressor: | paraffin oil Granular Suds 12% Silicone/silica, 18% stearyl alcohol, 70% |
| suppressor: | starch in granular form |
| Sulphate: | Anhydrous sodium sulphate |
| HMWPEO: | High molecular weight polyethylene oxide |
| TAE 25: | Tallow alcohol ethoxylate (25) |

DETERGENT EXAMPLE I

A granular fabric cleaning composition in accordance with the invention may be prepared as follows:

| Sodium linear $C_{12}$ alkyl benzene sulfonate | 6.5 |
| --- | --- |
| Sodium sulfate | 15.0 |
| Zeolite A | 26.0 |
| Sodium nitrilotriacetate | 5.0 |
| Enzyme of the invention | 0.1 |
| PVP | 0.5 |
| TAED | 3.0 |
| Boric acid | 4.0 |
| Perborate | 18.0 |
| Phenol sulphonate | 0.1 |
| Minors | Up to 100 |

DETERGENT EXAMPLE II

A compact granular fabric cleaning composition (density 800 g/l) in accord with the invention may be prepared as follows:

| 45AS | 8.0 |
| --- | --- |
| 25E3S | 2.0 |

-continued

| | |
|---|---|
| 25E5 | 3.0 |
| 25E3 | 3.0 |
| TFAA | 2.5 |
| Zeolite A | 17.0 |
| NaSKS-6 | 12.0 |
| Citric acid | 3.0 |
| Carbonate | 7.0 |
| MA/AA | 5.0 |
| CMC | 0.4 |
| Enzyme of the invention | 0.1 |
| TAED | 6.0 |
| Percarbonate | 22.0 |
| EDDS | 0.3 |
| Granular suds suppressor | 3.5 |
| water/minors | Up to 100% |

DETERGENT EXAMPLE III

Granular fabric cleaning compositions in accordance with the invention which are especially useful in the laundering of coloured fabrics were prepared as follows:

| | | |
|---|---|---|
| LAS | 10.7 | — |
| TAS | 2.4 | — |
| TFAA | — | 4.0 |
| 45AS | 3.1 | 10.0 |
| 45E7 | 4.0 | — |
| 25E3S | — | 3.0 |
| 68E11 | 1.8 | — |
| 25E5 | — | 8.0 |
| Citrate | 15.0 | 7.0 |
| Carbonate | — | 10.0 |
| Citric acid | 2.5 | 3.0 |
| Zeolite A | 32.1 | 25.0 |
| Na-SKS-6 | — | 9.0 |
| MNAA | 5.0 | 5.0 |
| DETPMP | 0.2 | 0.8 |
| Enzyme of the invention | 0.10 | 0.05 |
| Silicate | 2.5 | — |
| Sulphate | 5.2 | 3.0 |
| PVP | 0.5 | — |
| Poly (4-vinylpyridine)-N-Oxide/copolymer of vinyl-imidazole and vinyl-pyrrolidone | — | 0.2 |
| Perborate | 1.0 | — |
| Phenol sulfonate | 0.2 | — |
| Water/Minors | Up to 100% | |

DETERGENT EXAMPLE IV

Granular fabric cleaning compositions in accordance with the invention which provide "Softening through the wash" capability may be prepared as follows:

| | | |
|---|---|---|
| 45AS | — | 10.0 |
| LAS | 7.6 | — |
| 68AS | 1.3 | — |
| 45E7 | 4.0 | — |
| 25E3 | — | 5.0 |
| Coco-alkyl-dimethyl hydroxyethyl ammonium chloride | 1.4 | 1.0 |
| Citrate | 5.0 | 3.0 |
| Na-SKS-6 | — | 11.0 |
| Zeolite A | 15.0 | 15.0 |
| MA/AA | 4.0 | 4.0 |
| DETPMP | 0.4 | 0.4 |

-continued

| | | |
|---|---|---|
| Perborate | 15.0 | — |
| Percarbonate | — | 15.0 |
| TAED | 5.0 | 5.0 |
| Smectite clay | 10.0 | 10.0 |
| HMWPEO | — | 0.1 |
| Enzyme of the invention | 0.10 | 0.05 |
| Silicate | 3.0 | 5.0 |
| Carbonate | 10.0 | 10.0 |
| Granular suds suppressor | 1.0 | 4.0 |
| CMC | 0.2 | 0.1 |
| Water/Minors | Up to 100% | |

DETERGENT EXAMPLE V

Heavy duty liquid fabric cleaning compositions in accordance with the invention may be prepared as follows:

| | I | II |
|---|---|---|
| LAS acid form | — | 25.0 |
| Citric acid | 5.0 | 2.0 |
| 25AS acid form | 8.0 | — |
| 25AE2S acid form | 3.0 | — |
| 25AE7 | 8.0 | — |
| CFAA | 5 | — |
| DETPMP | 1.0 | 1.0 |
| Fatty acid | 8 | — |
| Oleic acid | — | 1.0 |
| Ethanol | 4.0 | 6.0 |
| Propanediol | 2.0 | 6.0 |
| Enzyme of the invention | 0.10 | 0.05 |
| Coco-aikyl dimethyl hydroxy ethyl ammonium chloride | — | 3.0 |
| Smectite clay | — | 5.0 |
| PVP | 2.0 | — |
| Waterl Minors | Up to 100% | |

Materials and Methods

Strains:

B. lentus 309 and 147 are specific strains of *Bacillus lentus*, deposited with the NCIB and accorded the accession numbers NCIB 10309 and 10147, and described in U.S. Pat. No. 3,723,250 incorporated by reference herein.

*E. coli* $MC_{1000}$ (M. J. Casadaban and S. N. Cohen (1980); J. Mol. Biol. 138 179–207), was made r⁻,m⁺ by conventional methods and is also described in U.S. patent application Ser. No. 039,298.

Plasmids:

pJS3: *E. coli-B. subtilis* shuttle vector containing a synthetic gene encoding for subtilase 309. (Described by Jacob Schiødt et al. in Protein and Peptide letters 3:39–44 (1996)).

pSX222: *B. subtilis* expression vector (Described in PCT/DK96/00207).

General Molecular Biology Methods:

Unless otherwise mentioned the DNA manipulations and transformations were performed using standard methods of molecular biology (Sambrook et al. (1989) Molecular cloning: A laboratory manual, Cold Spring Harbor lab., Cold Spring Harbor, NY; Ausubel, F. M. et al. (eds.) "Current protocols in Molecular Biology". John Wiley and Sons, 1995; Harwood, C. R., and Cutting, S. M. (eds.) "Molecular Biological Methods for Bacillus". John Wiley and Sons, 1990).

Enzymes for DNA manipulations were used according to the specifications of the suppliers.

Enzymes for DNA Manipulations

Unless otherwise mentioned all enzymes for DNA manipulations, such as e.g. restriction endonucleases, ligases etc., are obtained from New England Biolabs, Inc.

Construction of Random Mutagenized Libraries

Performing Localized Random Mutagenesis

A mutagenic primer (oligonucleotide) is synthesized which corresponds to the part of the DNA sequence to be mutagenized except for the nucleotide(s) corresponding to amino acid codon(s) to be mutagenized.

Subsequently, the resulting mutagenic primer is used in a PCR reaction with a suitable opposite primer. The resulting PCR fragment is purified and digested and cloned into the shuttle vector.

Alternatively and if necessary, the resulting PCR fragment is used in a second PCR reaction as a primer with a second suitable opposite primer so as to allow digestion and cloning of the mutagenized region into the shuttle vector. The PCR reactions are performed under normal conditions.

Proteolytic Activity

In the context of this invention proteolytic activity is expressed in Kilo NOVO Protease Units (KNPU). The activity is determined relatively to an enzyme standard (SAVINASE®), and the determination is based on the digestion of a dimethyl casein (DMC) solution by the proteolytic enzyme at standard conditions, i.e. 50° C., pH 8.3, 9 min. reaction time, 3 min. measuring time. A folder AF 220/1 is available upon request to Novo Nordisk A/S, Denmark, which folder is hereby included by reference.

A GU is a Glycine Unit, defined as the proteolytic enzyme activity which, under standard conditions, during a 15-minutes' incubation at 40° C., with N-acetyl casein as substrate, produces an amount of $NH_2$-group equivalent to 1 mmole of glycine.

Enzyme activity can also be measured using the PNA assay, according to reaction with the soluble substrate succinyl-alanine-alanine-proline-phenyl-alanine-para-nitrophenol, which is described in the Journal of American Oil Chemists Society, Rothgeb, T. M., Goodlander, B. D., Garrison, P. H., and Smith, L. A., (1988).

Fermentation:

Fermentation of subtilase enzymes was performed at 30° C. on a rotary shaking table (300 r.p.m.) in 500 ml baffled Erlenmeyer flasks containing 100 ml BPX medium for 5 days.

Consequently, in order to make an e.g. 2 liter broth 20 Erlenmeyer flasks were fermented simultaneously.

Assay to Test for Proteases with Increased Autoproteolytic Stability:

Samples containing protease are made by growing strains including reference strains in suitable media allowing expression of protease in either microtiter plates or shake flasks.

From each sample containing protease, aliquots are taken, to which are added 1/10 vol.2 M Glycin-NaOH buffer; pH 10.0, and the aliquots are incubated for 3 hours at 4° C. and 55° C., respectively.

After incubation the protease activities are determined using the substrate succinyl-alanine-alanine-para-nitrophenol (Suc-Ala-Ala-pNA) at 0.6 g/l in the following buffer:

150 mM KCl, 50 mM $Na_2B_4O_7$; pH adjusted to 9.0.

20 micro-l sample+180 micro-l substrate are mixed in wells of 96-well microtiter plate.

Color development is followed at 405 nm in a microplate reader.

Activities are determined using SAVINASE® as standard.

The residual activity of a sample is calculated as the protease activity of the aliquot incubated at 55° C. in percentage of the protease activity of the aliquot incubated at 4° C.

The proteases exhibiting increased residual activity are identified.

Media:

BPX: Composition (per Liter)

| | |
|---|---|
| Potato starch | 100 g |
| Ground barley | 50 g |
| Soybean flour | 20 g |
| $Na_2HPO_4$X 12 $H_2O$ | 9 g |
| Pluronic | 0.1 g |
| Sodium caseinate | 10 g |

The starch in the medium is liquefied with alpha-amylase and the medium is sterilized by heating at 120° C. for 45 minutes. After sterilization the pH of the medium is adjusted to 9 by addition of $NaHCO_3$ to 0.1 M.

EXAMPLES

For the generation of enzyme variants according to the invention the same materials and methods as described in i.a. WO 89/06279 (Novo Nordisk A/S), EP 130,756 (Genentech), EP 479,870 (Novo Nordisk A/S), EP 214,435 (Henkel), WO 87/04461 (Amgen), WO 87/05050 (Genex), EP application no. 87303761 (Genentech), EP 260,105 (Genencor), WO 88/06624 (Gist-Brocades NV), WO 88/07578 (Genentech), WO 88/08028 (Genex), WO 88/08033 (Amgen), WO 88/08164 (Genex), Thomas et al. (1985) *Nature*, 318 375–376; Thomas et al. (1987) *J. Mol. Biol.*, 193, 803–813; Russel and Fersht (1987) *Nature* 328 496–500. Other methods well established in the art may also be used.

Example 1

Construction and Expression of Enzyme Variants:

Subtilase 309 site-directed variants were made by the "Unique site elimination (USE)" or the "Uracil-USE" technique described respectively by Deng et al. (Anal. Biochem. 200:81–88 (1992)) and Markvardsen et al. (BioTechniques 18(3):371–372 (1995)).

The template plasmid was pJS3, or an analogue of this containing a variant of Subtilase 309, e.g. USE mutagenesis was performed on pJS3 analogue containing a gene encoding the Y167I+R170L variant with a oligonucleotide directed to the construct A194P variant resulting in a final Y167I+R170L+A194P Subtilase 309 variant.

The in pJS3 constructed Subtilase 309 variants was then subcloned into the *B. subtilis* pSX222 expression plasmid, using the restriction enzymes KpnI and MluI.

This construct was transformed into a competent *B. subtilis* strain and in order to purify the protease fermented as described above in a medium containing 10 microg/ml Chloramphenicol (CAM).

Example 2

Purification of Enzyme Variants:

This procedure relates to purification of a 2 liter scale fermentation of the Subtilisin 147 enzyme, the Subtilisin 309 enzyme or mutants thereof.

Approximately 1.6 liters of fermentation broth were centrifuged at 5000 rpm for 35 minutes in 1 liter beakers. The supernatants were adjusted to pH 6.5 using 10% acetic acid and filtered on Seitz Supra S100 filter plates.

The filtrates were concentrated to approximately 400 ml using an Amicon CH2A UF unit equipped with an Amicon S1Y10 UF cartridge. The UF concentrate was centrifuged and filtered prior to absorption at room temperature on a Bacitracin affinity column at pH 7. The protease was eluted from the Bacitracin column at room temperature using 25% 2-propanol and 1 M sodium chloride in a buffer solution with 0.01 dimethylglutaric acid, 0.1 M boric acid and 0.002 M calcium chloride adjusted to pH 7.

The fractions with protease activity from the Bacitracin purification step were combined and applied to a 750 ml Sephadex G25 column (5 cm dia.) equilibrated with a buffer containing 0.01 dimethylglutaric acid, 0.2 M boric acid and 0.002 m calcium chloride adjusted to pH 6.5.

Fractions with proteolytic activity from the Sephadex G25 column were combined and applied to a 150 ml CM Sepharose CL 6B cation exchange column (5 cm dia.) equilibrated with a buffer containing 0.01 M dimethylglutaric acid, 0.2 M boric acid, and 0.002 M calcium chloride adjusted to pH 6.5.

The protease was eluted using a linear gradient of 0–0.1 M sodium chloride in 2 liters of the same buffer (0–0.2 M sodium chloride in case of Subtilisin 147).

In a final purification step protease containing fractions from the CM Sepharose column were combined and concentrated in an Amicon ultrafiltration cell equipped with a GR81 PP membrane (from the Danish Sugar Factories Inc.).

By using the techniques of Example 1 for the construction and the above isolation procedure the following subtilisin 309 variants were produced and isolated:

| | |
|---|---|
| A: | Y167I + R170L + A133P |
| B: | Y167I + R170L + T134P |
| C: | Y167I + R170L + A133P + T134P |
| D: | Y167I + R170L + V104C + S132C |
| E: | Y167I + R170L + A108C + T134C |
| F: | Y167A + R170S + F189A |
| G: | Y167A + R170S + Y192A |
| H: | Y167A + R170S + Y192P |
| I: | Y167A + R170S + Y192A + A194P |
| J: | Y167A + R170S + Y192P + A194P |
| K: | Y167A + R170S + F189G |
| L: | Y167A + R170S + F189E |
| M: | Y167A + R170S + F189R |
| N: | Y167I + R170L |
| M: | Y167I + R170L + A194P |
| O: | Y167A + R170S + A194P |
| P: | Y167A + R170L + A194P |
| Q: | Y167A + R170N + A194P |
| R: | V104C + S132C + Y167I + R170L |
| S: | A108C + T134C + Y167I + R170L |

Example 3

Identification of Autolytic Cleavage Site:

A fraction of the SAVINASE® variant N: 167I+R170L (after purification as described above) was by SDS-PAGE analysis found to contain two bands supposedly originating from autolytic degradation. The bands migrated with Mr's of 12 kDa and 10 kDa, respectively. The N-terminal amino acid sequences of the peptides constituting these two bands were determined following SDS-PAGE and electroblotting onto a PVDF membrane.

The N-terminal amino acid sequence of the band migrating with Mr 12 kDa was found to be Ala-Gln-Ser-Val-Pro-Trp-Gly-Ile-Ser- which is identical to the N-terminal amino acid sequence of N:Y167I+R170L.

The N-terminal amino acid sequence of the band migrating with Mr 10 kDa was found to be Gly-Ala-Gly-Leu-Asp-Ile-Val-Ala-Pro- which is identical to the amino acid sequence of amino acid residues 187 to 195 in N:Y167I+R170L (residues 193 to 201 in BPN' numbering). This identifies the peptide bond between amino acid residues 186 and 187 in N:Y167I+R170L (residues 192 and 193 in BPN' numbering) as an autolytic cleavage site.

Matrix assisted laser desorption ionisation time-of-flight mass spectrometry of the fraction revealed that the masses of the two components were 12,997.5 KDa±13 KDa and 8,397.8 KDa±8 KDa, respectively.

The theoretical mass of the autolytic fragment consisting of amino acid residues 187 to 269 in N:Y167I+R170L (residues 193 to 275 in BPN' numbering) is 8,397.3 KDa thereby confirming that no other autolytic cleavages have occured C-terminal to residue 186.

Using the mass value of the larger fragment (12,997.5 KDa) it is possible to deduce that the other autolytic cleavage has occured between amino acid residues 130 and 131 in N:Y167I+R170L (residues 132 and 133 in BPN' numbering). The theoretical mass of the autolytic fragment consisting of amino acid residues 1 to 130 in N:Y167I+R170L (residues 1 to 132 in BPN' numbering) is 12,699.1 kDa.

To substantiate these findings of autolytic cleavage sites in N:Y167I+R170L, the protease was incubated in a concentration of 2 mg/ml in 0.1 M sodium phosphate, pH 7.5 at 37° C. At various time points from 0 min to 6 hours a 20 microliter aliqout of the incubation mixture was withdrawn and added 80 microliters 1% TFA resulting in an irreversible inhibition of the proteolytic activity of N:Y167I+R170L. The samples were kept in the freezer until analysis by matrix assisted laser desorption time-of-flight mass spectrometry.

The result of the mass spectrometry clearly showed a steady increase in the amount of fragments with masses of 12,698.9 kDa±13 kDa and 8,396.1 kDa±8 kDa, respectively, and a steady decrease in the component with mass 26,607.0 KDa±26 kDa. The theoretical mass of N:Y167I+R170L is 26,605.4 kDa.

Example 4

Construction of Random Protease Variants

Three random libraries was constructed in the vicinity of the autoproteolytic claevage site 132–133. In each of the 3 libraries the BLS309 variant Y167I+R170L was used as template.

The construction of the 3 libraries of amino acids (aa) 1) 129–131, 2)132–133, 3)134–135 were prepared as described in Materials and Methods above.

One oligonucleotide was synthesized with 25% of each of the four bases in the first and the second base at amino acid codons wanted to be mutagenized. The third nucleotide (the wobble base) in codons were synthesized with 50%G/50%C to give a larger likelihood for changes to amino acids with one or two codons.

The mutagenic primer was used in a PCR reaction with a suitable opposite primer and the plasmid pJS3:(Y167I+R170L) as template. The resulting PCR fragment were purified and the resulting PCR fragment was used in a second PCR reaction as a primer with a second suitable opposite primer. This step was advantageous to be able to digest and clone the mutagenized region into the pJS3 shuttle vector.

Libraries of region 129–131, 132–133,134–135 have been prepared containing from 10,000 to 80,000 clones/library.

Ten randomly chosen colonies were sequenced to confirm the mutations designed.

Example 5

Identification of Protease Variants with Increase Autoproteolytic Activity

The clones in each library constructed as described in example 4 is tested for autoproteolytic stability as described above.

For each library 500 individual clones are incubated in a microtiter plate overnight at 37° C. in 200 microliters LB medium with 10 microg/ml Chloramphenicol (CAM).

With the SAVINASE® variant N:Y167I+R170L as reference strain two variants with relative increased autoproteolytic stability was identified X:A133D+Y167I+R170L, Y: P129K+Y167I+R170L, and GG:P129K+P131H+Y167I+R170L.

This illustrates that the substitutions (P129K, P131H, A133D) in the vicinity of the autoproteolytic cleavage site located between 132–133 provide increased autoproteolytic stability.

Example 6

Comparative Fermentation Experiment with Variant(s) with Increased Autoproteolytic Stability The SAVINASE® variant "M: Y167I+R170L+A194P" was in a fermentation experiment compared to its precursor variant "N: Y167I+R170L" not having the A194P substitution in the vicinity of the autoproteolytic split site located between residues 192–193.

Both variants were cloned in a pSX222 expression vector background and fermented as described above in a 100 ml BPX medium containing 10 microg/ml CAM.

After 5 days fermentation 1.5 ml of the BPX fermentation medium was centrifuged and the supernatant was used to measure the Proteolytic activity (KPNU) as described above.

The fermentation medium containing the "M: Y167I+R170L+A194P" variant had a significant higher level of proteolytic activity as compared to the fermentation medium containing the "N: Y167I+R170L" variant.

It is presently believed that both variants have the same specific activity, and consequently it is presently believed that the higher Proteolytic activity level in the fermentation medium containing the "M: Y167I+R170L+A194P" variant is due to a relatively increased autoproteolytic stability in the "M: Y167I+R170L+A194P" variant compared to the "N: Y167I+R170L" precurs variant not having the A194P substitution.

Similar results were obtained with the variants O:Y167A+R170S+A194P, P:Y167A+R170L+A194P, and Q:Y167A+R170N+A194P compared with their corresponding precursor variant without the A194P mutation.

Further, similar results were obtained with the variant HH: A133P+Y167A+R170S compared with its corresponding precursor variant without the A133P mutation, showing that the substitution A133P give increased autoproteolytic activity.

The invention claimed is:

1. A modified subtilase comprising a substitution at position 134 and a substitution at position 190, wherein each position is numbered according to the amino acid sequence of the mature subtilisin BPN' of SEQ ID NO: 36 and the modified subtilase has protease activity.

2. The modified subtilase of claim 1, further comprising a substitution at one or more of positions 129, 130, 131, and 133.

3. The modified subtilase of claim 2, comprising one or more substitutions selected from the group consisting of:
   (a) a substitution at position 129 with F, I, L, M, or V; and
   (b) a substitution at position 131 with F, I, L, M, or V.

4. The modified subtilase of claim 1, further comprising a substitution at one or more of positions 159, 184, 185, 187, 170, and 171.

5. The modified subtilase of claim 4, comprising one or mare of the following mutations:
   (a) a substitution at position 159 with F, I, L, M, or V;
   (b) a substitution at position 164 with F, I, L, M, or V;
   (c) a substitution at position 167 with A, C, F, G, H, I, L, M, N, P, Q, S, T, V, or W;
   (d) a substitution at position 170 with A, C, F, G, H, I, L, M, N, P, Q, S, T, V, W, or Y; and
   (e) a substitution at position 171 with A, C, F, G, H, I, L, M, N, P, Q, S, T, V, or W.

6. The modified subtilase of claim 1, further comprising a substitution at position 189.

7. The modified subtilase of claim 1, comprising at least one further mutation at one or more other positions, wherein said further mutation is selected from the group consisting of a substitution, insertion or deletion.

8. The modified subtilase of claim 7, wherein the one or more other positions are selected from the group consisting of: 27, 36, 57, 76, 97, 101, 104, 120, 123, 206, 218, 222, 224, 235 and 274.

9. The modified subtilase of claim 8, wherein the subtilase is an I-S2 sub-group subtilase and the at least one further mutation is selected from the group consisting of K27R, *36D S57P, N76D, G97N, S101G, V104A, V104N, V104Y, H120D, N123S, Q206E, N218S, M222A, M222S, T224S, K235L, and T274A.

10. The modified subtilase of claim 9, wherein the one at least one further mutation is selected from the group consisting of K27R+V104Y+N123S+T274A, N76D+V104A, V104N+S101G, and any other combination of K27R, N76D, S101G, V104A, V104N, V104Y, N123S, and T274A.

11. The modified subtilase of claim 1, wherein the subtilase is a sub-group I-S1 subtilase.

12. The modified subtilase of claim 11, wherein the subtilase is subtilisin I168, subtilisin BPN', subtilisin DY, or subtilisin Carlsberg.

13. The modified subtilase of claim 1, wherein the subtilase is a sub-group I-S2 subtilase.

14. The modified subtilase of claim 13, wherein the subtilase is subtilisin 147, subtilisin 309, subtilisin PB92, or subtifisin YaB.

15. The modified subtilase of claim 13, wherein the subtilase is thermitase.

16. A detergent composition comprising a modified subtilase of claim 1 and a surfactant.

17. The detergent composition of claim 16, which additionally comprises an amylase, cellulase, cutinase, lipase, oxidoreductase, or another protease.

18. A DNA sequence encoding a modified subtilase of claim 1.

19. A vector comprising a DNA sequence of claim 18.

20. A microbial host cell transformed with a vector of claim 19.

21. A method for producing a modified subtilase, comprising
   (a) culturing a host of claim 20 under conditions conducive to the expression and secretion of the modified subtilase, and
   (b) recovering the modified subtilase.

* * * * *

SEQUENCE LISTING

<160> NUMBER OF SEQ ID NOS: 35

<210> SEQ ID NO 1
<211> LENGTH: 49
<212> TYPE: PRT
<213> ORGANISM: Bacillus amyloliquifaciens

<400> SEQUENCE: 1

Gly Gly Pro Ser Gly Ser Ala Ala Leu Lys Ala Ala Val Asp Lys Ala
 1               5                  10                  15

Val Ala Ser Glu Gly Thr Ser Gly Ser Ser Ser Thr Val Gly Tyr Pro
            20                  25                  30

Gly Lys Tyr Pro Phe Ser Ser Val Gly Pro Glu Leu Asp Val Met Ala
        35                  40                  45

Pro

<210> SEQ ID NO 2
<211> LENGTH: 49
<212> TYPE: PRT
<213> ORGANISM: Bacillus subtilis

<400> SEQUENCE: 2

-continued

```
Gly Gly Pro Thr Gly Ser Thr Ala Leu Lys Thr Val Asp Lys Ala
 1               5                  10                  15

Val Ser Ser Glu Gly Ser Ser Gly Ser Thr Ser Thr Val Gly Tyr Pro
                20                  25                  30

Ala Lys Tyr Pro Phe Ser Ser Ala Gly Ser Glu Leu Asp Val Met Ala
            35                  40                  45

Pro

<210> SEQ ID NO 3
<211> LENGTH: 49
<212> TYPE: PRT
<213> ORGANISM: Bacillus subtilis

<400> SEQUENCE: 3

Gly Gly Pro Ser Gly Ser Thr Ala Leu Lys Gln Ala Val Asp Lys Ala
 1               5                  10                  15

Tyr Ala Ser Ser Gly Ser Ser Gly Ser Gln Asn Thr Ile Gly Tyr Pro
                20                  25                  30

Ala Lys Tyr Asp Phe Ser Ser Val Gly Ala Glu Leu Glu Val Met Ala
            35                  40                  45

Pro

<210> SEQ ID NO 4
<211> LENGTH: 49
<212> TYPE: PRT
<213> ORGANISM: Bacillus licheniformis

<400> SEQUENCE: 4

Gly Gly Pro Ser Gly Ser Thr Ala Met Lys Gln Ala Val Asp Asn Ala
 1               5                  10                  15

Tyr Ala Arg Ser Gly Ser Ser Gly Asn Thr Asn Thr Ile Gly Tyr Pro
                20                  25                  30

Ala Lys Tyr Asp Phe Ser Ser Val Gly Ala Glu Leu Glu Val Met Ala
            35                  40                  45

Pro

<210> SEQ ID NO 5
<211> LENGTH: 45
<212> TYPE: PRT
<213> ORGANISM: Bacillus alcalohilus

<400> SEQUENCE: 5

Gly Ser Pro Ser Pro Ser Ala Thr Leu Glu Gln Ala Val Asn Ser Ala
 1               5                  10                  15

Thr Ser Arg Ser Gly Ala Gly Ser Ile Ser Tyr Pro Ala Arg Tyr Ala
                20                  25                  30

Phe Ser Gln Tyr Gly Ala Gly Leu Asp Ile Val Ala Pro
            35                  40                  45

<210> SEQ ID NO 6
<211> LENGTH: 45
<212> TYPE: PRT
<213> ORGANISM: Bacillus YaB

<400> SEQUENCE: 6

Gly Ser Ser Ala Gly Ser Ala Thr Met Glu Gln Ala Val Asn Gln Ala
 1               5                  10                  15

Thr Ala Ser Ser Gly Ala Gly Asn Val Gly Phe Pro Ala Arg Tyr Ala
                20                  25                  30
```

Phe Ser Gln Tyr Gly Ala Gly Leu Asp Ile Val Ala Pro
            35                  40                  45

<210> SEQ ID NO 7
<211> LENGTH: 45
<212> TYPE: PRT
<213> ORGANISM: Bacillus lentus

<400> SEQUENCE: 7

Gly Ser Thr Ser Gly Ser Ser Thr Leu Glu Leu Ala Val Asn Arg Ala
1               5                   10                  15

Asn Asn Ala Thr Gly Arg Gln Gly Val Asn Tyr Pro Ala Arg Tyr Ser
            20                  25                  30

Phe Ser Thr Tyr Gly Pro Glu Ile Glu Ile Ser Ala Pro
            35                  40                  45

<210> SEQ ID NO 8
<211> LENGTH: 46
<212> TYPE: PRT
<213> ORGANISM: Bacillus subtilis

<400> SEQUENCE: 8

Gly Thr Thr Ser Asp Ser Lys Ile Leu His Asp Ala Val Asn Lys Ala
1               5                   10                  15

Tyr Glu Gln Asp Gly Asn Gly Lys Pro Val Asn Tyr Pro Ala Ala Tyr
            20                  25                  30

Ser Phe Ser Thr Thr Gly Asp Glu Val Glu Phe Ser Ala Pro
            35                  40                  45

<210> SEQ ID NO 9
<211> LENGTH: 50
<212> TYPE: PRT
<213> ORGANISM: Thermoactinomyces vulgaris

<400> SEQUENCE: 9

Gly Gly Pro Ser Asp Val Pro Glu Leu Glu Glu Ala Val Lys Asn Ala
1               5                   10                  15

Val Lys Asn Glu Gly Asp Gly Asp Glu Arg Thr Glu Glu Leu Ser Tyr
            20                  25                  30

Pro Ala Ala Tyr Asn Phe Ser Asn Ala Asn Lys Glu Ile Asp Leu Val
            35                  40                  45

Ala Pro
    50

<210> SEQ ID NO 10
<211> LENGTH: 45
<212> TYPE: PRT
<213> ORGANISM: Bacillus amyloliquifaciens

<400> SEQUENCE: 10

Gly Gly Thr Val Gly Asn Ser Gly Leu Gln Gln Ala Val Asn Tyr Ala
1               5                   10                  15

Trp Asn Lys Ala Gly Asn Thr Ala Pro Asn Tyr Pro Ala Tyr Tyr Ser
            20                  25                  30

Phe Ser Thr Tyr Gly Ser Trp Val Asp Val Ala Ala Pro
            35                  40                  45

<210> SEQ ID NO 11
<211> LENGTH: 47
<212> TYPE: PRT

-continued

<213> ORGANISM: Dichelobacter nodosus

<400> SEQUENCE: 11

```
Gly Gly Gly Gly Gly Cys Ser Gln Asn Ser Gln Arg Met Ile Asp Lys
 1               5                  10                  15

Thr Thr Asn Leu Glu Asn Gln Asp Ala Ser Arg Thr Trp Pro Ser Ser
            20                  25                  30

Cys Asn Phe Ser Asn Tyr Gly Ala Arg Val His Leu Ala Ala Pro
        35                  40                  45
```

<210> SEQ ID NO 12
<211> LENGTH: 47
<212> TYPE: PRT
<213> ORGANISM: Xanthomonus campestris

<400> SEQUENCE: 12

```
Gly Gly Gly Gly Ser Cys Ser Thr Thr Met Gln Asn Ala Ile Asn Gly
 1               5                  10                  15

Ala Val Ser Arg Asp Ala Ser Asn Val Ser Gly Ser Leu Pro Ala Asn
            20                  25                  30

Cys Ala Tyr Ser Asn Phe Gly Thr Gly Ile Asp Val Ser Ala Pro
        35                  40                  45
```

<210> SEQ ID NO 13
<211> LENGTH: 58
<212> TYPE: PRT
<213> ORGANISM: Bacillus subtilis

<400> SEQUENCE: 13

```
Gly Gly Gly Ser Gly Leu Asp Glu Trp Tyr Arg Asp Met Val Asn Ala
 1               5                  10                  15

Trp Arg Ala Ala Thr Asp Leu Phe Ile Pro Gly Gly Pro Gly Ser Ile
            20                  25                  30

Ala Asn Pro Ala Asn Tyr Pro Phe Ser Leu Gln Gly Pro Ser Pro Tyr
        35                  40                  45

Asp Glu Ile Lys Pro Glu Ile Ser Ala Pro
    50                  55
```

<210> SEQ ID NO 14
<211> LENGTH: 59
<212> TYPE: PRT
<213> ORGANISM: Enterococcus faecalis

<400> SEQUENCE: 14

```
Gly Ser Tyr Lys Asn Met Glu Ile Asp Asp Glu Arg Phe Thr Val Glu
 1               5                  10                  15

Ala Phe Arg Lys Val Val Asn Tyr Ala Arg Lys Asn Glu Ser Arg Asp
            20                  25                  30

Ile Ser Thr Gly Asn Glu Lys His Ile Pro Gly Gly Leu Glu Tyr Ser
        35                  40                  45

Asn Tyr Gly Ser Asn Val Ser Ile Tyr Gly Pro
    50                  55
```

<210> SEQ ID NO 15
<211> LENGTH: 68
<212> TYPE: PRT
<213> ORGANISM: Staphylococcus epidermis

<400> SEQUENCE: 15

```
Gly Asn Val Leu Ile Arg Asp Asp Glu Lys Val Asp Tyr Asp Ala Leu
```

-continued

```
                1               5                  10                 15
Gly Lys Ala Ile Asn Tyr Ala Gln Lys Lys Asp Gly Ile Asn Val Lys
                        20                  25                 30

Lys Val Lys Glu Ile Asn Lys Lys Arg Thr Ser Lys Lys Val Tyr Asp
                35                  40                 45

Ser Pro Ala Asn Leu Asn Phe Ser Asn Tyr Gly Asn Asn Phe Ile Asp
        50                  55                 60

Leu Met Thr Ile
65
```

<210> SEQ ID NO 16
<211> LENGTH: 71
<212> TYPE: PRT
<213> ORGANISM: Streptococcus pyogenes

<400> SEQUENCE: 16

```
Gly Asn Ala Ala Leu Ala Tyr Ala Asn Leu Pro Asp Glu Thr Lys Lys
  1               5                  10                 15

Ala Phe Asp Tyr Ala Lys Ser Lys Asp Ser Ser Phe Gly Gly Lys Thr
                20                  25                 30

Arg Leu Pro Leu Ala Asp His Pro Asp Tyr Gly Val Val Gly Thr Pro
        35                  40                 45

Ala Ala Ala Asp Phe Ser Ser Trp Gly Leu Thr Ala Asp Gly Asn Ile
    50                  55                 60

Lys Pro Asp Ile Ala Ala Pro
65                  70
```

<210> SEQ ID NO 17
<211> LENGTH: 73
<212> TYPE: PRT
<213> ORGANISM: Lactococcus lactis

<400> SEQUENCE: 17

```
Gly Ser Asn Ser Gly Asn Gln Thr Leu Glu Asp Pro Glu Leu Ala Ala
  1               5                  10                 15

Val Gln Asn Ala Asn Glu Ser Ser Gly Thr Ser Gly Ser Ala Thr Glu
                20                  25                 30

Gly Val Asn Lys Asp Tyr Tyr Gly Leu Gln Asp Asn Glu Met Val Gly
        35                  40                 45

Ser Pro Gly Thr Ser Arg Phe Thr Ser Tyr Gly Pro Val Ser Asn Leu
    50                  55                 60

Ser Thr Lys Pro Asp Ile Thr Ala Pro
65                  70
```

<210> SEQ ID NO 18
<211> LENGTH: 63
<212> TYPE: PRT
<213> ORGANISM: Serratia marcescens

<400> SEQUENCE: 18

```
Gly Ile Ala Pro Asp Gln Pro Val Pro Thr Gly His Ser Ala Met
  1               5                  10                 15

Ser Thr Leu Leu Arg Ala Ala Arg His Tyr Asn Asn Tyr Asn Ile Pro
                20                  25                 30

Glu Ala Gln Lys Ser Leu Pro Tyr Ala Phe Pro Asp Val Leu Asn Ser
        35                  40                 45

Ser Thr Ser Cys Gly Gln Thr Ala Ser Tyr Cys Val Ser Ala Pro
    50                  55                 60
```

<210> SEQ ID NO 19
<211> LENGTH: 54
<212> TYPE: PRT
<213> ORGANISM: Anabaena variabilis

<400> SEQUENCE: 19

Gly Gly Pro Asp Gly Lys Gln Lys Val Pro Leu Pro Asp Ser Thr Arg
1               5                   10                  15

Leu Ala Met Asp Tyr Ala Ile Asn Lys Gly Gly Asn Glu Ser Val Asp
            20                  25                  30

Asn Asp Gly Tyr Ala Ser Tyr Glu Lys Tyr Ser Asp Phe Gly Thr Ala
        35                  40                  45

Val Trp Cys Ala Phe Pro
    50

<210> SEQ ID NO 20
<211> LENGTH: 58
<212> TYPE: PRT
<213> ORGANISM: Mus

<400> SEQUENCE: 20

Gly Pro Asn Asp Asp Gly Lys Thr Val Glu Gly Pro Gly Arg Leu Ala
1               5                   10                  15

Gln Lys Ala Phe Glu Tyr Gly Val Lys Gln Gly Gly Arg Gln Gly
            20                  25                  30

Asp Asn Cys Asp Cys Asp Gly Tyr Thr Asp Ser Ile Tyr Tyr Ala Glu
        35                  40                  45

Lys Cys Ser Ser Thr Leu Ala Thr Ser Tyr
    50                  55

<210> SEQ ID NO 21
<211> LENGTH: 57
<212> TYPE: PRT
<213> ORGANISM: Homo sapiens

<400> SEQUENCE: 21

Gly Thr Pro Asp Asn Gly Lys Thr Val Asp Gly Pro Arg Asp Val Thr
1               5                   10                  15

Leu Gln Ala Met Ala Asp Gly Val Asn Lys Gly Gly Ser Tyr Asp
            20                  25                  30

Asp Cys Asn Cys Asp Gly Tyr Ala Ser Ser Met Trp Tyr Asp Glu Ser
        35                  40                  45

Cys Ser Ser Thr Leu Ala Ser Thr Phe
    50                  55

<210> SEQ ID NO 22
<211> LENGTH: 58
<212> TYPE: PRT
<213> ORGANISM: Homo sapiens

<400> SEQUENCE: 22

Gly Pro Glu Asp Asp Gly Lys Thr Val Asp Gly Pro Ala Arg Leu Ala
1               5                   10                  15

Glu Glu Ala Phe Phe Arg Gly Val Ser Gln Gly Gly Arg Glu His
            20                  25                  30

Asp Ser Cys Asn Cys Asp Gly Tyr Thr Asn Ser Ile Tyr Tyr Ser Glu
        35                  40                  45

Ala Cys Ser Ser Thr Leu Ala Thr Thr Tyr

<210> SEQ ID NO 23
<211> LENGTH: 58
<212> TYPE: PRT
<213> ORGANISM: Drosophila melanogaster

<400> SEQUENCE: 23

Gly Pro Asp Asp Gly Lys Thr Val Asp Gly Pro Gly Glu Leu Ala
 1               5                  10                  15

Ser Arg Ala Phe Ile Glu Gly Thr Thr Lys Gly Gly Gly Arg Glu Gln
            20                  25                  30

Asp Asn Cys Asn Cys Asp Gly Tyr Thr Asn Ser Ile Trp Tyr Ser Glu
        35                  40                  45

Lys Cys Ser Ser Thr Leu Ala Thr Thr Tyr
    50                  55

<210> SEQ ID NO 24
<211> LENGTH: 58
<212> TYPE: PRT
<213> ORGANISM: Kluyveromyces lactis

<400> SEQUENCE: 24

Gly Pro Ser Asp Asp Gly Lys Thr Met Gln Ala Pro Asp Thr Leu Val
 1               5                  10                  15

Lys Lys Ala Ile Ile Lys Gly Val Thr Glu Gly Gly Gly Met Phe Gly
            20                  25                  30

Asp Ser Cys Asn Phe Asp Gly Tyr Thr Asn Ser Ile Phe Tyr Ser Glu
        35                  40                  45

Ser Cys Ser Ala Val Met Val Val Thr Tyr
    50                  55

<210> SEQ ID NO 25
<211> LENGTH: 58
<212> TYPE: PRT
<213> ORGANISM: Saccharomyces cerevisiae

<400> SEQUENCE: 25

Gly Pro Ala Asp Asp Gly Arg His Leu Gln Gly Pro Ser Asp Leu Val
 1               5                  10                  15

Lys Lys Ala Leu Val Lys Gly Val Thr Glu Gly Gly Gly Thr Arg Gly
            20                  25                  30

Asp Asn Cys Asn Tyr Asp Gly Tyr Thr Asn Ser Ile Tyr Tyr Ser Glu
        35                  40                  45

Gly Cys Ser Ala Val Met Ala Val Thr Tyr
    50                  55

<210> SEQ ID NO 26
<211> LENGTH: 45
<212> TYPE: PRT
<213> ORGANISM: Vibrio alginolyticus

<400> SEQUENCE: 26

Gly Gly Gly Gln Ser Val Ala Leu Asp Ser Ala Val Gln Ser Ala Val
 1               5                  10                  15

Gln Ser Ser Asn Ala Asp Ala Cys Asn Tyr Ser Pro Ala Arg Val Ala
            20                  25                  30

Phe Ser Asn Trp Gly Ser Cys Val Asp Val Phe Ala Pro
        35                  40                  45

-continued

```
<210> SEQ ID NO 27
<211> LENGTH: 45
<212> TYPE: PRT
<213> ORGANISM: Thermus rT41A

<400> SEQUENCE: 27

Gly Gly Gly Ala Ser Thr Ala Leu Asp Thr Ala Val Met Asn Ala Ile
1               5                   10                  15

Asn Ala Asp Asn Arg Asp Ala Cys Phe Tyr Ser Pro Ala Arg Val Thr
            20                  25                  30

Phe Ser Asn Tyr Gly Arg Cys Leu Asp Leu Phe Ala Pro
        35                  40                  45

<210> SEQ ID NO 28
<211> LENGTH: 45
<212> TYPE: PRT
<213> ORGANISM: Thermus aquaticus

<400> SEQUENCE: 28

Gly Gly Gly Val Ser Thr Ala Leu Asp Asn Ala Val Lys Asn Ser Ile
1               5                   10                  15

Ala Ala Asp Asn Ala Asn Ala Cys Asn Tyr Ser Pro Ala Arg Val Ala
            20                  25                  30

Phe Ser Asn Tyr Gly Ser Cys Val Asp Leu Phe Ala Pro
        35                  40                  45

<210> SEQ ID NO 29
<211> LENGTH: 45
<212> TYPE: PRT
<213> ORGANISM: Tritirachium album Limber

<400> SEQUENCE: 29

Gly Gly Gly Tyr Ser Ser Ser Val Asn Ser Ala Ala Ala Arg Leu Gln
1               5                   10                  15

Ser Ser Asn Asn Ala Asp Ala Arg Asn Tyr Ser Pro Ala Ser Glu Pro
            20                  25                  30

Phe Ser Asn Tyr Gly Ser Val Leu Asp Ile Phe Gly Pro
        35                  40                  45

<210> SEQ ID NO 30
<211> LENGTH: 45
<212> TYPE: PRT
<213> ORGANISM: Tritirachium album

<400> SEQUENCE: 30

Gly Gly Gly Tyr Ser Ser Ser Val Asn Ser Ala Ala Ala Asn Leu Gln
1               5                   10                  15

Gln Ser Asn Asn Ala Asp Ala Arg Asn Tyr Ser Pro Ala Ser Glu Ser
            20                  25                  30

Phe Ser Asn Tyr Gly Ser Val Leu Asp Ile Phe Ala Pro
        35                  40                  45

<210> SEQ ID NO 31
<211> LENGTH: 46
<212> TYPE: PRT
<213> ORGANISM: Tritirachium album

<400> SEQUENCE: 31

Gly Gly Gly Pro Ser Ser Ser Ala Val Asn Arg Ala Ala Ala Glu Ile
1               5                   10                  15
```

```
Thr Ser Ala Glu Ala Thr Asp Ala Ser Ser Ser Pro Ala Ser Glu
         20                  25                  30

Glu Tyr Ser Asn Phe Gly Ser Val Val Asp Leu Leu Ala Pro
         35                  40                  45
```

<210> SEQ ID NO 32
<211> LENGTH: 45
<212> TYPE: PRT
<213> ORGANISM: Acremonium chrysogenum

<400> SEQUENCE: 32

```
Gly Gly Gly Tyr Ser Ser Ala Phe Asn Asn Ala Val Asn Thr Ala Tyr
 1               5                  10                  15

Ser Arg Asp Asn Gln Asn Ala Ala Asn Tyr Ser Pro Ala Ser Ala Ala
         20                  25                  30

Phe Ser Asn Tyr Gly Ser Val Leu Asp Ile Phe Ala Pro
         35                  40                  45
```

<210> SEQ ID NO 33
<211> LENGTH: 45
<212> TYPE: PRT
<213> ORGANISM: Aspergillus oryzae

<400> SEQUENCE: 33

```
Gly Gly Gly Tyr Ser Lys Ala Phe Asn Asp Ala Val Glu Asn Ala Phe
 1               5                  10                  15

Glu Gln Glu Asn Ser Asp Ala Gly Gln Thr Ser Pro Ala Ser Ala Pro
         20                  25                  30

Phe Ser Asn Phe Gly Lys Val Val Asp Val Phe Ala Pro
         35                  40                  45
```

<210> SEQ ID NO 34
<211> LENGTH: 45
<212> TYPE: PRT
<213> ORGANISM: Saccharomyces cerevisiae

<400> SEQUENCE: 34

```
Gly Gly Gly Lys Ser Pro Ala Leu Asp Leu Ala Val Asn Ala Ala Val
 1               5                  10                  15

Glu Val Glu Asn Gln Asp Ala Cys Asn Thr Ser Pro Ala Ser Ala Asp
         20                  25                  30

Phe Ser Asn Trp Gly Lys Cys Val Asp Val Phe Ala Pro
         35                  40                  45
```

<210> SEQ ID NO 35
<211> LENGTH: 51
<212> TYPE: PRT
<213> ORGANISM: Yarrowia lipolytica

<400> SEQUENCE: 35

```
Gly Gly Pro Lys Ser Ala Ser Gln Asp Ala Leu Trp Ser Arg Ala Thr
 1               5                  10                  15

Gln Glu Asp Ala Val Asp Ala Cys Asn Asp Ser Pro Gly Asn Ile Gly
         20                  25                  30

Gly Trp Ser Gly Gly Gln Gly Ser Asn Tyr Gly Thr Cys Val Asp Val
         35                  40                  45

Phe Ala Pro
 50
```